US007825225B2

(12) United States Patent
Plested et al.

(10) Patent No.: US 7,825,225 B2
(45) Date of Patent: Nov. 2, 2010

(54) VACCINE

(75) Inventors: Joyce Susan Plested, Oxford (GB); Michael Paul Jennings, Queensland (AU); Margaret Ann Jaqueline Gidney, Ottawa (CA); Andrew David Cox, Ottawa (CA); James Clare Richards, Ottawa (CA); Edward Richard Moxon, Oxford (GB)

(73) Assignee: Isis Innovation Ltd., Oxford (GB)

( * ) Notice: Subject to any disclaimer, the term of this patent is extended or adjusted under 35 U.S.C. 154(b) by 0 days.

(21) Appl. No.: 12/508,691

(22) Filed: Jul. 24, 2009

(65) Prior Publication Data

US 2010/0016560 A1 Jan. 21, 2010

Related U.S. Application Data

(62) Division of application No. 10/089,583, filed as application No. PCT/GB00/03758 on Oct. 2, 2000, now Pat. No. 7,585,510.

(60) Provisional application No. 60/196,305, filed on Apr. 12, 2000, provisional application No. 60/156,940, filed on Sep. 30, 1999.

(51) Int. Cl.
*C12P 21/08* (2006.01)
*C12N 5/07* (2010.01)
*A61K 39/40* (2006.01)

(52) U.S. Cl. ................. 530/388.4; 530/387.5; 435/329; 435/354; 435/340; 424/150.1; 424/164.1

(58) Field of Classification Search ....................... None
See application file for complete search history.

*Primary Examiner*—S. Devi
(74) *Attorney, Agent, or Firm*—Thomas, Kayden, Horstemeyer & Risley, LLP; David J. Hayzer

(57) ABSTRACT

The invention relates to a vaccine for the treatment of disease caused by *Neisseria*, the vaccine including one or more immunogenic components for *Neisseria* serogroups, as well as antibodies to the immunogenic components and methods of preventing and treating *Neisseria* infections. The immunogens are based on elements of the inner core lipopolysaccharide.

1 Claim, 15 Drawing Sheets

STRATEGY DIAGRAM
(Methods used in brackets)

↓

Identify antibody accessible epitopes of
wild-type encapsulated Gp B Nm strains (2,3,4)

↓

Investigation of conservation of antibody accessible
inner core epitopes in natural population of Nm (3)

↓

Investigate the structure of
LPS derived from Nm of known mab activity

↓

Define details of conserved
antibody accessible epitopes (2,5)

↓

Select minmum number of glycoforms having
range of epitopes representative of all Nm strains (3,4,5)

↓

Investigate potential of glycoform to elicit functional
antibodies (e.g. bacterial, opsonophagcytic & animal
protection assays)

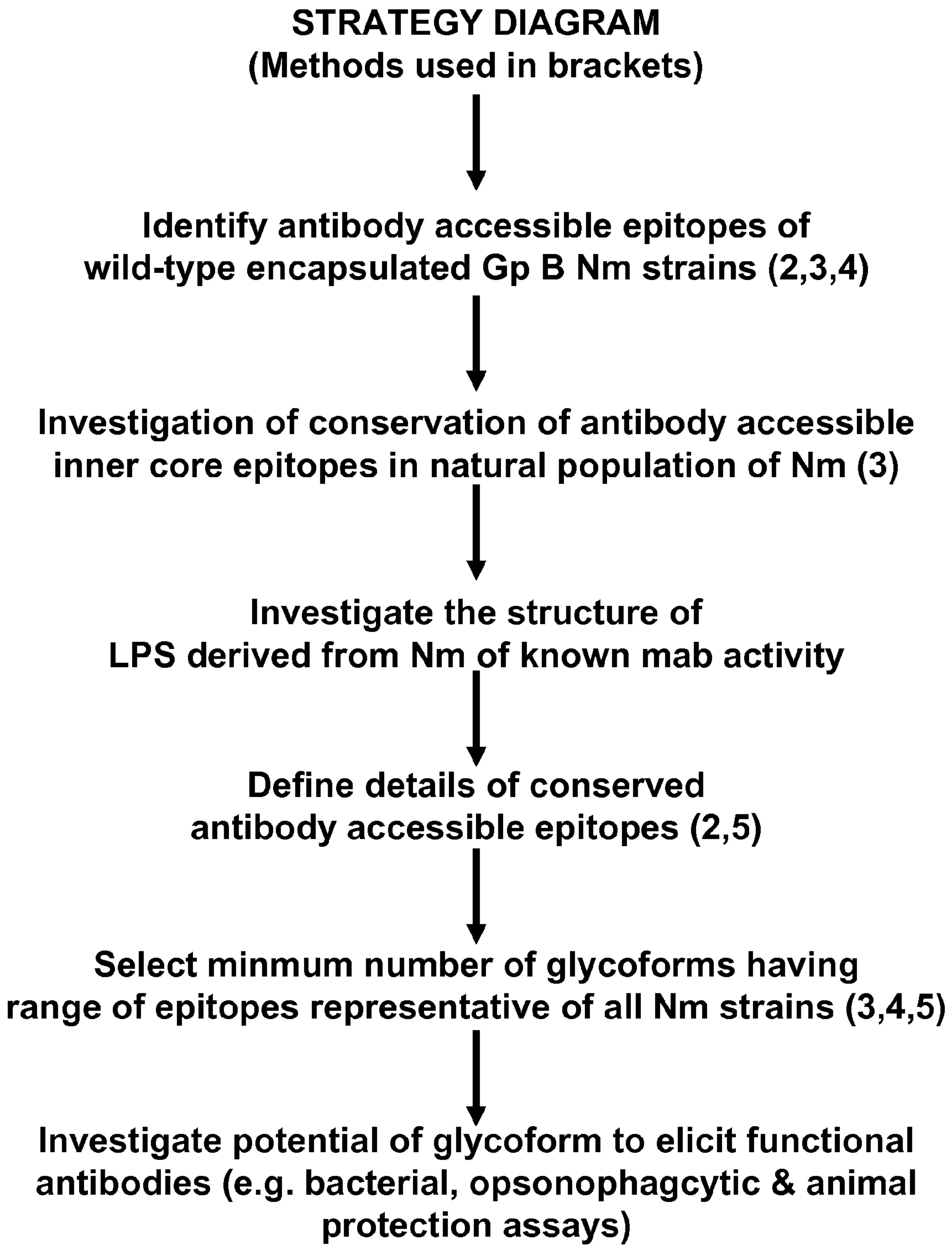

*Fig. 9*

VACCINE

CROSS-REFERENCE TO RELATED APPLICATIONS

This application is a Divisional of U.S. patent application entitled "Vaccine", filed on Jul. 11, 2002 and assigned Ser. No. 10/089,583, now U.S. Pat. No. 7,585,510, which claimed the benefit of PCT/GB00/03758 filed Oct. 2, 2000, which claimed the benefit of U.S. provisional patent application 60/196,305, filed Apr. 12, 2000 and U.S. provisional patent application 60/156,940, filed Sep. 30, 1999.

TECHNICAL FIELD

The present invention relates to vaccines against *Neisseria* infection, especially to infection by pathogenic *Neisseria meningitidis* and *Neisseria gonorrhoeae.*

BACKGROUND OF THE INVENTION

Septicaemia and meningitis caused by *Neisseria meningitidis* remain a global health problem, especially in young children. *Neisseria meningitidis* is usually a commensal of the nasopharynx, the only major natural reservoir of this organism. The virulence factors that potentiate the capacity of *Neisseria meningitidis* to cause invasive disease include capsular polysaccharides, pili (fimbrae) or outer membrane proteins and lipopolysaccharides (DeVoe, I. W. 1982. Microbiol. Rev. 46: 162-190; Jennings, H. J. 1989. Contrib. Microbiol. Immunol. 10: 151-165; Tonjum, T., and M. Koomey. 1997. Gene 192: 155-163; Nassif, X., et al., 1997. Gene 192: 149-153; Poolman, J. T. 1996. Adv. Exp. Med. Biol. 397: 73-33; Verheul, A. F., et al., 1993. Microbiol. Rev. 57: 34-49; Preston, A, et al., 1996 Crit. Rev. Microbiol. 22: 139-180).

Existing licensed vaccines against capsular serogroups A, C, W and X are available (Frasch, C. E. 1989. Clin. Microbiol. Rev. 2 Suppl: S134-138; Herbert, M. A., et al., 1995. Commun. Dis. Reg. CDR Rev. 5: R130-135; Rosenstein, N., et al., 1998. J.A.M.A. 279: 435-439), but generally lack satisfactory immunogenicity in very young children and do not induce long lasting protective immunity (Peltola, H., et al., 1977. New Engl. J. Med. 297: 686-691; Peltola, H., et al., 1985. Pediatrics 76: 91-96; Reingold, A. L., et al., 1985. Lancet II:114-118; Lepow, M. L., et al., 1986. J. Infect. Dis. 154: 1033-1036; Cadoz, M. 1998. Vaccine 16: 1391-1395). Nonetheless, their utility has been significant in affording protection to selected populations such as the military, travelers and those at exceptional risk in outbreaks or epidemics (CDC. 1990. MMWR Morb. Mortal. Wkly. Rep. 39, No. 42: 763). Very recently, meningococcal conjugate Group C vaccines have been introduced as a routine immunization in the United Kingdom.

The major public health priority concerning invasive meningococcal infections is to identify Group B vaccines that are highly effective in infants and give long term protection. Group B strains have accounted for a substantial, often a majority of invasive *Neisseria meningitidis* infections in many countries in Europe and North America (CDR. 1997 April. Communicable Disease Weekly Report. 7, No. 14). Prevention of Group B invasive disease represents a particularly difficult challenge in vaccine development as the capsular polysaccharide is very poorly immunogenic and even conjugates have shown disappointing immunogenicity (Jennings, H. J., and H. C. Lugowski. 1981. J. Immunology 127: 1011-1018). Further, there are concerns about the safety of vaccines whose rationale is to induce antibodies to the Group B polysaccharide, a homopolymer of α-linked 2-8 neuraminic acid. The identical polysialicacid (PSA) is a post translational modification of a glycoprotein present on human cells, especially neurons, the latter is referred to as neural cell adhesion molecule (N-CAM) (Finne, J., et al., 1983. Lancet 2: 355-357). Both theoretical and experimental evidence have been used to argue that the induction of antibodies might result in autoimmune, pathological damage to host tissues.

Alternative approaches to develop vaccine candidates against Group B *Neisseria meningitidis* are being actively explored. These include: outer membrane porins (Poolman, J. T., et al., 1995. Meningococcal disease, p. 21-34K. Cartwright (ed.). John Wiley and sons, Wetzler, L. M. 1994. Ann. N.Y. Acad. Sci. 730: 367-370; Rosenquist E., et al., 1995. Infect. Immun. 63:4642-4652; Zollinger, W. D., et al., 1997. Infect. Immun. 65: 1053-1060), transferrin binding proteins (Al'Aldeen, A. A., and K. A. Cartwright. 1996. J. Infect. 33: 153-157) and lipopolysaccharides (Verheul, A. F., et al., 1993. Infect. Immun. 61: 187-196; Jennings, H. J., et al., 1984. Infect. Immun. 43: 407-412; Jennings, H. J., et al., 987. Antonie Van Leeuwenhoek 53: 519-522; Gu, X. X., and C. M. Tsai. 1993. Infect. Immun. 61: 1873-1880; Moxon, E. R., et al., 1998. Adv. Exp. Med. Biol. 435: 237-243).

The structure of *Neisseria meningitidis* LPS has been studied in considerable detail by Jennings H. and co-workers with additional contributions by others (Griffiss, J. M. et al., 1987 Infect. Immun. 55: 1792-1800; Stephens, D. S., et al., 1994. Infect. Immun. 62: 2947-2952; Apicella, M. A., et al., 1994. Methods Enzymol. 235: 242-252; Poolman, J. T. 1990. Polysaccharides and membrane vaccines, p. 57-86. in Bacterial Vaccines, A. Mizrahi (ed.)., et al. 1997. FEMS Microbiol Lett. 146: 247-253). The structures of major glycoforms for several immunotypes (L1-L9) have been published L1, L6 (Di Fabio, J. L., et al., 1990. Can. J. Chem. 68: 1029-1034; Wakarchuk, W. W., et al., 1998. Eur. J. Biochem. 254: 626-633); L3 (Pavliak, V., et al., 1993. J. Biol. Chem. 268: 14146-14152); L5 (Michon, F., et al. 1990. J. Biol. Chem. 265:7243-7247); L2 (Gamian, A., et al., 1992. J. Biol. Chem. 267: 922-925); L4,L7 (Kogan, G., et al., 1997. Carbohydr. Res. 298: 191-199): L8 (Wakarchuk, W. W., et al., 1996, J. Biol. Chem. 271, 19166-19173), L9 (Jennings, H. J., et al., 1983. Carbohydr. Res. 21: 233-241). Reference is also made to the following discussion of the accompanying FIG. 1.

It is known that, in addition to this inter-strain variation, individual *Neisseria meningitidis* strains exhibit extensive phase variation of outer core LPS structures (reviewed in van Putten, J. P., and B. D. Robertson. 1995. Mol. Microbiol. 16: 847-853 and Andersen, S. R., et al., 1997. Microb. Pathog. 23: 139-155). The molecular mechanism of this intra strain variation involves hypermutable loci within the reading frames encoding several glycosyl transferases (Gotschlich, E. C. 1994. J. Expt. Med. 180: 2181-2190, Jennings, M. P., et al., 1995. Mol. Microbiol. 18: 729-740). Similar mechanisms of phenotypic variation have been reported for other phase-variable surface components of pathogenic *Neisseria*, including Opc (Sakari, J., et al., 1994. Mol. Microbiol. 13: 207-217), Opa (Stem, A., et al., 1986. Cell 47: 61-71) and PDC proteins (Jonsson, A. B., et al., 1991. EMBO. J. 10: 477-488). The high frequency, reversible molecular switching is mediated by homopolymeric tracts of cytosines or guanines through slippage-like mechanisms that results in frame shifts (Gotschlich, E. C. 1994. J. Expt. Med. 180: 2181-2190, Jennings, M. P., et al., 1995. Mol. Microbiol. 18: 729-740; Stern, A. and T. F. Meyer. 1987. Mol. Microbiol. 1: 5-12).

Despite the extensive antigenic variation of LPS, the inner core of the LPS has been considered to be relatively highly conserved, and therefore the use of the inner core of the LPS structure has been suggested for use in vaccine design. However, the problems with candidate vaccine generation in this way are numerous.

First, although it was known that certain components of the inner core could be immunogenic (Jennings, H. J. et al., 1984. Infect. Immun. 43: 407-412; Verheul, A. F., et al., 1991. Infect. Immun. 59: 3566-3573), the extent of conservation of these epitopes across the diversity of meningococcal disease isolates was not known and evidence of bactericidal activity of antibodies to these epitopes has not been shown. U.S. Pat. No. 5,705,161 discloses that oligosaccharides of meningococcal immunotypes differ, for example, with regard to monosaccharide composition, amount and location of phosphoethanolamine groups and degree of acetylation of the inner core GlcNAc unit or other units, indicating that many possible structures may be found in the core structure. U.S. Pat. No. 5,705,161 also suggests that a portion of the core of a meningococcal LPS may be suitable for use in a vaccine, although no specific immunogenic epitopes or supporting data are disclosed.

Secondly, given the presence of the outer core LPS structure and other surface exposed non-LPS structures; including capsule, it is not known whether the inner core structure is accessible to the immune system to allow a bactericidal immune response to be generated. Furthermore, any vaccine would need to contain immunogenic structures which elicit an immune response to the complete range of pathogenic *Neisseria meningitidis* strains. However, the extent of variation exhibited by the inner core structure of virulent strains is not known, and rigorous investigation of the problem has not been undertaken.

Furthermore, in the publication New Generation Vaccines (1997, Ed. M. M. Levine, publ. Marcel Deker Inc, New York, Chapter 34, page 481), it is stated that, with respect to vaccine development, "including LPS that consists only of the common inner core region of the oligosaccharide may not result in induction of bactericidal antibodies.".

In addition, other species of the genus *Neisseria* pose global health problems. For example, *Neisseria gonorrhoeae* is involved in sexually transmitted diseases such as urethritis, salpingitis, cervicitis, proctitis and pharyngitis, and is a major cause of pelvic inflammatory disease in women.

Accordingly, there is still a need in the art for an effective vaccine against pathogenic *Neisseria* infection, such as *Neisseria meningitidis* and *Neisseria gonorrhoeae* infection.

The present invention sets out to address this need.

SUMMARY OF THE INVENTION

In a first aspect, the invention relates to a vaccine for the treatment of disease caused by *Neisseria* infection, the vaccine comprising an immunogenic component of *Neisseria* strains. The vaccine presents a conserved and accessible epitope that in turn promotes a functional and protective response.

We have now discovered that the inner core of the LPS of *Neisseria* can be used to generate a protective immune response to *Neisseria* infections, for example *Neisseria meningitidis* infections. For simplicity the present invention is herein exemplified principally by discussion of vaccines and treatments against *Neisseria meningitidis* infections, but the invention extends to diseases caused by other pathogenic *Neisseria* species.

Using a range of novel monoclonal antibodies, epitopes belonging to the inner core of *Neisseria meningitidis* have been identified which have been found to be accessible to the immune system, and which are capable of stimulating the production of functional, protective antibodies. Moreover, analysis of *Neisseria meningitidis* strains using the new antibody tools indicates that certain epitopes are common to a range of *Neisseria meningitidis* disease isolates, and sometimes occur in a majority of such strains. Accordingly a vaccine comprising only a limited range of *Neisseria meningitidis* inner core epitopes can provide effective immunoprophylaxis against the complete range of strains causing *Neisseria meningitidis* infection. Similar considerations apply to other pathogenic species.

In a related aspect, the invention provides a vaccine effective against strains of the bacteria of the genus *Neisseria*, especially strains of the species *Neisseria meningitidis*. Particularly in the latter instance, the vaccine comprises one or more immunogens which can generate antibodies that recognize epitopes in encapsulated strains. The one or more immunogens represent one or more accessible inner core epitopes. Thus, the immunogens can give rise to antibodies that recognize a majority of strains.

We use the word "principal" to refer to a majority. Thus, a principal immunogenic component elicits antibodies to a majority of strains.

In our approach, antibodies were generated by immunizing mice using *Neisseria meningitidis* galE mutants. The antibodies produced were specific to the LPS inner core because galE mutants lack outer core structures. The reactivity of these antibodies against a panel of *Neisseria meningitidis* strains representative of the diversity found in natural populations of disease isolates was investigated. One monoclonal antibody reacted with 70% of all *Neisseria meningitidis* strains tested, suggesting strong conservation of the inner core epitope recognized by this antibody, termed antibody B5. The epitope against which B5 reacts has been characterized and can be used to form the basis of a vaccine to prevent *Neisseria* infections.

A hybridoma producing the monoclonal antibody B5, designated hybridoma NmL3B5, has been deposited under the Budapest Treaty on 26 Sep. 2000 with the International Depositary Authority of Canada in Winnipeg, Canada, and given the Accession Number IDAC 260900-1.

In this way, we have obtained proof in principle that one or more of the inner core epitopes of LPS are conserved and accessible to antibodies, that a specific immune response to these epitopes can mediate protection, and that LPS inner core oligosaccharides can be candidate vaccines. The inner core LPS typically consists of an inner core oligosaccharide attached to lipid A, with the general formula as shown:

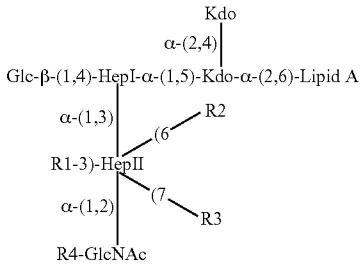

where R1 is a substituent at the 3-position of HepII, and is hydrogen or Glc-α-(1, or phosphoethanolamine; R2 is a substituent at the 6-position of HepII, and is hydrogen or phosphoethanolamine; R3 is a substituent at the 7-position of HepII, and is hydrogen or phosphoethanolamine, and R4 is acetyl or hydrogen at the 3-position, 4-position or 6-position of the GlcNAc residue, or any combination thereof; and where Glc is D-glucopyranose; Kdo is 3-deoxy-D-manno-2-octulosonic acid; Hep is L-glycero-D-manno-heptose, and GlcNAc is 2-acetamido-2-deoxy-D-glucopyranose.

BRIEF DESCRIPTION OF THE DRAWINGS

The present invention is now illustrated by the following Figures and Examples which are not limiting upon the present invention, wherein:

FIG. 1A illustrates the LPS structure of *Neisseria meningitidis* immunotypes that are Mab B5 positive.

FIG. 1B illustrates the LPS structure of *Neisseria meningitidis* immunotypes that are Mab B5 negative.

FIG. 3A illustrates the molecular model of the calculated (MMC) lowest energy state of the core oligosaccharide from galE mutant of L3. Kdo in grey, Heptose (Hep) in red, Glucose (Glc) and Glucosamine (GlcNAc) in light and darker green, (PEtn) in brown.

FIG. 3B illustrates the molecular model of the calculated (MMC) lowest energy state of the core oligosaccharide from galE mutant of L4. Kdo in grey, Heptose (Hep) in red, Glucose (Glc) and Glucosamine (GlcNAc) in light and darker green, (PEtn) in brown.

FIG. 3C illustrates the molecular model of the calculated (MMC) lowest energy state of the core oligosaccharide from galE mutant of L8 dephosphorylated. Kdo in grey, Heptose (Hep) in red, Glucose (Glc) and Glucosamine (GlcNAc) in light and darker green, (PEtn) in brown.

FIG. 5A: Fluorescein tagging with rabbit polyclonal antibody specific for Group B *Neisseria meningitidis* capsule. FIG. 5B: rhodamine tagging of MAb B5, specific for galE LPS (×2400 magnification). Confocal immunofluorescence microscopy of in vivo grown MC58 organisms stained as described in Plested et al., 1999. Infect. Immunity 67, 5417-5426. FIG. 5C: anti-capsular antibody. FIG. 5D: MAb B5 (×2400 magnification).

FIG. 6A: Silver-stained tricine gel of LPS preparations (10 μg/lane) from *Neisseria meningitidis* Group B strains which were not reactive with MAb B5. These LPS preparations were either not treated (−) or treated with (+) neuraminidase to show the presence of sialic acid. MAb B5 negative strains: Lanes 1, 2=NGE30; lanes 3, 4=BZ157; lanes 5, 6=EG328; lanes 7, 8=1000; lanes 9, 10=3906.

FIG. 6B: Silver-stained tricine gel of LPS preparations (10 μg/lane) from *Neisseria meningitidis* Group B strains which were not reactive with MAb B5. These LPS preparations were either not treated (−) or treated with (+) neuraminidase to show the presence of sialic acid. MAb B5 negative strains: Lanes 1, 2=EG327; lanes 3.4=NGH38; lanes 5, 6=NGH15; MAb B5 positive strain: lanes 7, 8=MC58. Presence of sialic acid (NeuAc) indicated by +. This band was seen in untreated (−) and removed in treated (+) neuraminidase preparations.

FIGS. 7A-7C illustrates accessibility of the LPS epitope to A4 in *Neisseria meningitidis* whole cells. MAb A4 accesses the inner core LPS epitope in *Neisseria meningitidis* L4 galE mutant in the presence of capsule (magnification ×100). *Neisseria meningitidis* L4 galE adherent to epithelial cells (16HBE140) stained with:

FIG. 7A: *Neisseria meningitidis* L4 galE adherent to epithelial cells (16HBE140) stained with MAb A4 (anti-mouse TRITC-red).

FIG. 7B: *Neisseria meningitidis* L4 galE adherent to epithelial cells (16HBE140) stained with anti-cap B (anti-rabbit FITC-green).

FIG. 7C: *Neisseria meningitidis* L4 galE adherent to epithelial cells (16HBE140) stained with triple staining with MAb A4 (anti-Mouse TRITC-red), anti-cap B (anti-rabbit FITC-green) and epithelial cells stained DAPI (blue).

FIG. 7D: *Neisseria meningitidis* L3 MC58 adherent to HUVECs stained with MAb B5 (antimouse TRITC-red)

FIG. 7E: *Neisseria meningitidis* L3 MC58 adherent to HUVECs stained with MAb B5 anti-cap B (anti-rabbit FITC-green) using confocal immunofluorescence microscopy.

FIG. 9 illustrates the strategy for the Example 2.

DETAILED DESCRIPTION

Figure 1A:
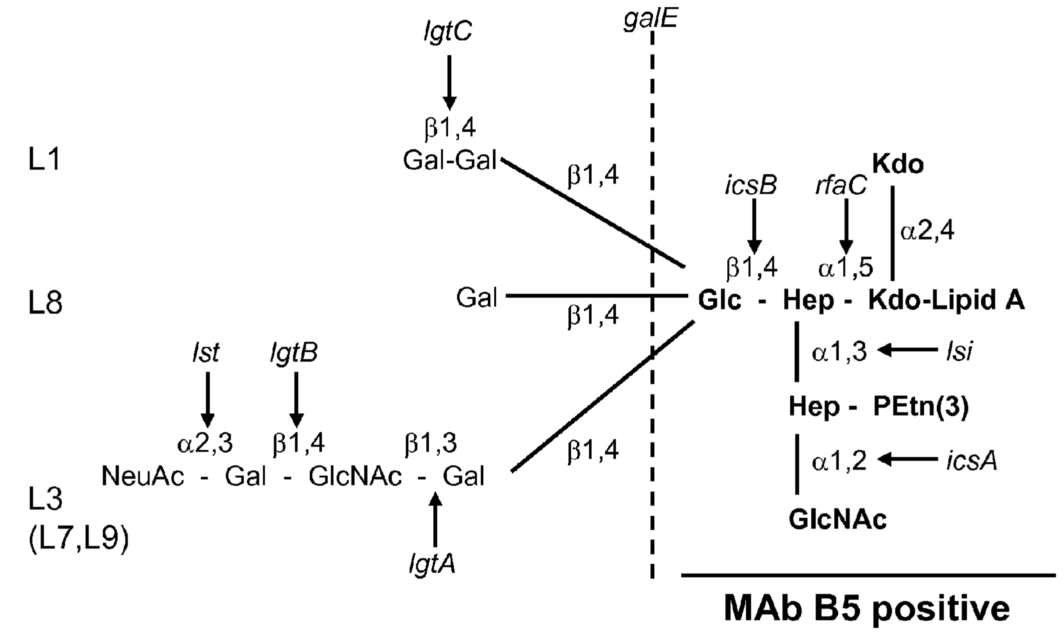
FIGS. 1A and 1B show representations of the structure of meningococcal LPS oligosaccharides of immunotypes L1-L9. Immunotypes are indicated to the extreme left. The vertical dotted line marks the junction between the inner core structures to the right and outer core structures to the left. The epitope recognized by MAb B5 is indicated in bold (MAb B5 positive). Arabic numerals indicate the linkage between sugars or amino-sugars. Alpha and beta indicate the carbon 1 linkage at the non-reducing end of the sugar. Genes for incorporating each of the key sugars or amino-sugars into the LPS oligosaccharide in the biosynthetic pathway are indicated with arrows indicating where in the pathway the gene product is required. Abbreviations include: Kdo, 2-keto-2-deoxyoctulosonic acid; PEtn, phosphoethanolamine; Gal, galactose: GLcNAc, N-acetyl glucosamine; Glc, glucose; Hep, Heptose. Immunotype L5 has no PEtn on the second heptose. The gene that adds the glucose to the second heptose (IgtG) is phase variable.

The principal immunogenic component for *Neisseria meningitidis* strains is preferably a single immunogenic component found in at least 50% of *Neisseria meningitidis* strains, i.e. in the majority of naturally occurring *Neisseria meningitidis* strains. The principal immunogenic component forms a candidate vaccine immunogen. Preferably the immunogenic component of the vaccine of the present invention is any one element or structure of *Neisseria meningitidis* or other species of *Neisseria* capable of provoking an immune response, either alone or in combination with another agent such as a carrier. Preferably the principal immunogenic component comprises of or consists of an epitope which is a part or all of the inner core structure of the *Neisseria meningitidis* LPS. The immunogenic component may also be derived from this inner core, be a synthetic version of the inner core, or be a functional equivalent thereof such as a peptide mimic. The inner core LPS structure of *Neisseria meningitidis* is generally defined as that shown in FIGS. 1A and 1B and as outlined in the figure legends. The immunogenic component is suitably one which elicits an immune response in the presence and in the absence of outer core LPS.

The principal immunogenic component is conserved in at least 50% of *Neisseria* strains within the species, preferably at least 60%, and more preferably at least 70%. Reactivity with 100% strains is an idealized target, and so the immunogenic component typically recognizes at most 95%, or 85% of the strains. Conservation is suitably assessed functionally, in terms of antibody cross-reactivity. We prefer that the immunogenic component is present in at least 50% of serogroup B strains, preferably at least 60%, more preferably at least 70%, even more preferably at least 76%. Suitably, assessment of the cross reactivity of the immunogenic component is made using a representative collection of strains, such those outlined in Maiden (Maiden M. C. J., et al., 1998. P.N.A.S.195, 3140-3145).

Preferably the principal immunogenic component is found in the *Neisseria meningitidis* immunotype L3, and preferably it is not in L2. More specifically, we prefer that the immunogen is found in the immunotypes L1, L3, L7, L8 and L9, but not in L2, L4, L5 or L6. In other words, we prefer that the immunogen, notably the principal immunogenic component, generates antibodies which are reactive with at least the L3 immunotype, and usually the L1, L3, L7, L8 and L9 immunotypes, but not with L2, and usually not the L2, L4, L5 and L6 immunotypes. There are conformational differences forced on the inner core of the L2 and L3 immunotypes by different arrangements at HepII, namely the PEtn moiety at the 6-position in L2 or at the 3-position in L3, and the Glc residue at the 3-position in L2. Currently we do not envisage the possibility of a single epitope for both L2 and L3 immunotypes. In other words, without dismissing the possibility of a single epitope, the present invention is expected to require different immunogens to elicit antibodies for L2 and L3.

Preferably the principal immunogenic component is a conserved epitope on the LPS inner core recognized by an antibody termed B5 herein. The preferred epitope of the invention is thus any epitope recognized by the B5 antibody.

Preferably the immunogenic component is a conserved epitope on the LPS inner core defined by the presence of a phosphoethanolamine moiety (PEtn) linked to the 3-position of HepII, the β-chain heptose, of the inner core, or is a functional equivalent thereof. In this respect, where the context permits, HepI and HepII refer to the heptose residues of the inner core oligosaccharide which respectively are proximal and distal to the lipid A moiety of the neisserial LPS, without being necessarily tied to the general formula given above.

Preferably this epitope comprises a glucose residue on HepI, the α-chain heptose residue. While this glucose is not necessary for B5 biding, it is required for optimal recognition.

The principal immunogenic component of the present invention is preferably an epitope on the LPS inner core which comprises an N-acetyl glucosamine on HepII. The presence of N-acetyl glucosamine is required for optimal recognition by B5.

Preferably the principal immunogenic component comprises both the N-acetyl glucosamine on HepII and a glucose residue on HepI.

The immunogenic component of the present invention is typically only limited by the requirement for a phosphoethanolamine moiety (PEtn) linked to the 3-position of HepII of the inner core, which is required for B5 reactivity. The structure of the inner core may be modified, replaced, or removed, as necessary, to the extent that these are not needed. Similarly, any outer core structures may be modified or deleted, to the extent that structural elements are not needed. There is no requirement for the immunogenic component to lack the outer core portion, or equivalent, of the LPS. The immunogenic component may comprise outer core elements having a galactose component, for example the terminal galactose residue of the lacto-N-neotetraose. In one suitable embodiment, the immunogenic component is derived from LPS and is free from other cellular material. Alternatively, cellular material may be present, and can take the form of live or killed bacteria.

In a related aspect, the vaccine of this invention has an immunogenic epitope recognized by an antibody to a galE mutant of *Neisseria meningitidis.*

In a further embodiment the vaccine suitably comprises further immunogenic elements from the inner core with an aim to achieving up to 100% coverage. Preferably the vaccine comprises only a limited number (4-6, or less) of immunogenic elements, more preferably only those glycoforms which are representative of all possible PEtn positions on HepII, the β-chain heptose, of the inner core, i.e. wherein PEtn is at the 3-position, exocyclic (6-position or 7-position) or absent, with or without an α-1-3 linked glucose at HepII, or a combination thereof. The presence of PEtn substituent is not required for the generation of antibodies by an immunogenic component of this invention.

Moreover, as detailed herein, the epitopes of this invention are immunogenic and accessible, and thus can be used to develop an effective vaccine. Furthermore, as detailed herein, a vaccine containing only a limited number of glycoforms (representing all the possible PEtn positions on HepII, namely position 3-, or 6- or 7-, or none, and combinations thereof), is able to effectively provide protection against the diverse range of meningococcal isolates causing invasive disease.

Accordingly the vaccine of the present invention preferably comprises an epitope which is defined by the presence of a phosphoethanolamine moiety (PEtn) linked to the 3-position of HepII of the inner core, and additionally comprises an epitope defined by the presence of PEtn on the 6-position of HepII of the inner core, and/or an epitope defined by PEtn on the 7-position of HepII of the inner core, or wherein there is no additional PEtn addition. Preferably the vaccine contains only immunogenic components which are these inner core glycoform variants.

The B5 antibody of the present invention also recognizes the inner core structures of *Neisseria gonorrhoeae* and *Neisseria lactamica*. As such, the invention extends to any *Neisseria* species, and any reference to *Neisseria meningitidis* can, as appropriate, be extended to other *Neisseria* species, preferably *Neisseria meningitidis, Neisseria gonorrhoeae*, and *Neisseria lactamica*, most preferably *Neisseria meningitidis*. The invention also extends to immunogenic components in other *Neisseria* species which are related to those identified in *Neisseria meningitidis*, either by function, antibody reactivity or structure. The invention is not limited to pathogenic strains of *Neisseria*. The vaccine of this invention can be derived from a commensal strain of *Neisseria*, especially a strain of *Neisseria lactamica*. The species *Neisseria lactamica* is typically strongly immunogenic, and therefore we prefer that the LPS inner core immunogenic component is derived from this species.

The vaccine may thus be homologous or heterologous, and thus founded on an immunogenic component from the target micro-organism, homologous, or from a different micro-organism, heterologous. The micro-organism can be naturally occurring or not, such as can be produced by recombinant techniques. In particular, the micro-organism can be engineered to modify the epitope or to modify other components.

In a further aspect of the invention we have determined that a second monoclonal antibody, herein termed A4, is able to react with inner core epitopes of nearly all of the *Neisseria meningitidis* strains which do not react with the B5 antibody. Thus, of the 100 *Neisseria meningitidis* strains tested, 30% were not reactive with B5 and were found to lack a PEtn moiety at the 3-position of Hepli. Of these 30 strains, 27 were reactive with A4. Accordingly, a vaccine comprising only 2 inner core epitopes, corresponding to those epitopes defined by cross reactivity with A4 and B5, provides 97% coverage of a representative collection of *Neisseria meningitidis* strains, preferably as assessed by using the collection of strains as outlined in Maiden et al.[supra]. A preferred epitope of the invention is thus also any epitope recognized by the A4 antibody.

A hybridoma producing the monoclonal antibody A4, designated hybridoma NmL4galEA4, has been deposited under the Budapest Treaty on 26 Sep. 2000 with the International Depositary Authority of Canada in Winnipeg, Canada, and given the Accession Number IDAC 260900-2.

The present invention thus also relates to a vaccine comprising a few immunogenic components, wherein at least 70% of *Neisseria meningitidis* strains of the species possess at least one of the immunogenic components, preferably 80%, preferably 90%, and most preferably 97%. In this way the vaccine can give protective coverage against *Neisseria* infection in 70%, preferably 80%, 90% or even 97% or more of cases.

A few immunogenic components suitably means at least two immunogenic components, preferably only 2. More generally the few components comprise 2 to 6 components, such as 2, 3, 4, 5, or 6 components, more suitably 2, 3, or 4 components. Preferably the immunogenic components are a few glycoforms of the inner core, representative of all natural *Neisseria meningitidis* strains. In this way, a vaccine containing a limited number of glycoforms can give approaching 100% coverage of *Neisseria meningitidis* strains.

Figure 3A:
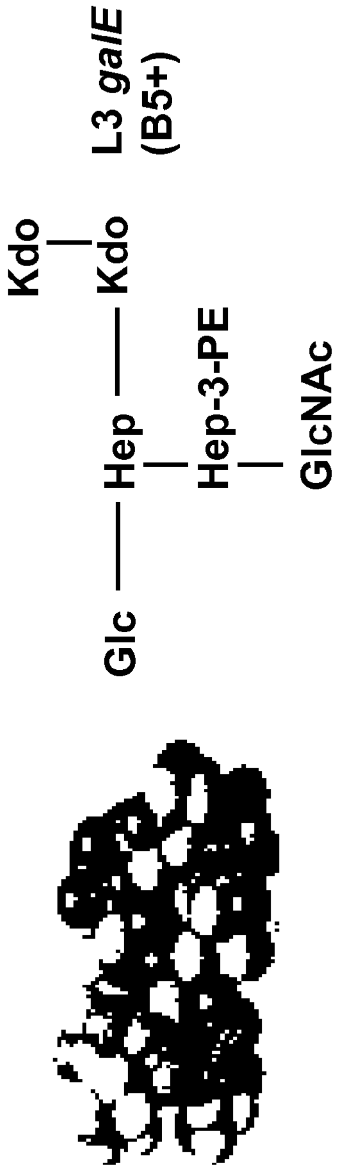
FIGS. 3A-3C illustrate space-filling 3-D molecular models of the calculated (MMC) lowest energy states of the core oligosaccharide from galE mutants of L3, L4, and L8 dephosphorylated. Kdo moiety indicated in grey is substituted at the O-5 position by the heptose disaccharide inner core unit (red), HepI provides the point via a glucose residue (dark green) for extension to give α-chain epitopes, while HepII is substituted by N-acetyl glucosamine residue (lighter green) at 0-2. PEtn (brown) is shown in 0-3 position in L3 immunotype and 0-6 in L4 immunotype. Colour versions of this and the other figures for Example 1 are to be found in Plested et al., 1999 Infect. Immunity 67, 5417-5426.
Figure 3B:
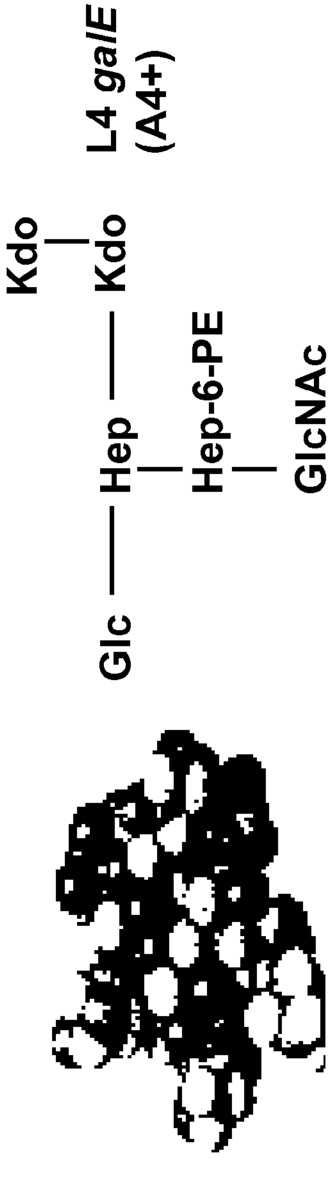
Figure 3C:
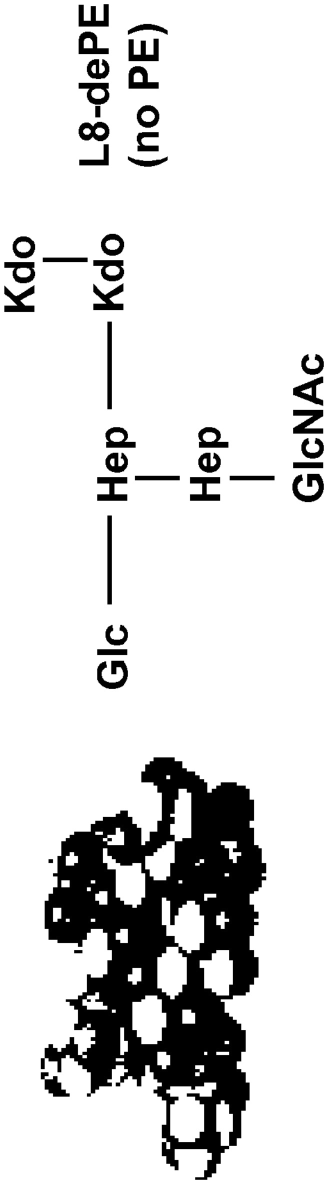

A representation of the 3D structures of the LPS inner core having a PEtn moiety at the 3-position, 6-position or absent at HepII are shown in FIGS. 3A-3C. Accordingly, the present invention also extends to immunogenic elements which have the same or similar structures to these inner core structures, as defined by their 3D geometry and to antibodies capable of interacting with such structures, either as assessed in vitro, in vivo or in silico.

The immunogenic elements of the invention are preferably those shown to elicit antibodies having opsonic and bactericidal activity, and shown to generate antibodies which confer passive protection in in vivo models.

The invention also extends to use of any immunogenic element as defined above in the preparation of a medicament for the prevention, treatment or diagnosis of *Neisseria* infection.

The candidate vaccine immunogens of the present invention may be suited for the prevention of all *Neisseria* infections. However, a vaccine for the treatment of *Neisseria meningitidis* is preferred, with a vaccine for group B strains especially preferred.

Preferably the immunogenic element of the vaccine is accessible in the presence of bacterial capsule. Accordingly, antibodies generated by an individual who is vaccinated will be able to access the same epitope on invading strains of

*Neisseria*, and thus protect the individual from infection. Antibodies given directly to a patient for treatment also are thus able to directly access the target *Neisseria* strains.

Preferably the vaccine of the present invention comprises epitopes which are capable of stimulating antibodies which are opsonic. We further prefer that these antibodies are capable of binding to wild type *Neisseria* strains to confer protection against infection and which are bactericidal.

The present invention also provides a method for treating pathogenic *Neisseria*. The method employs one or a few immunogenic components which give rise to effective antibodies and which rely on an inner core epitope for stimulating the immune response. The immune response is ordinarily B cell mediated, but we can include T cell mediated immunity. The antibodies generated by the vaccine of this invention bind to inner core elements of the pathogenic target bacterium.

Diseases caused by *Neisseria meningitidis* include principally meningitis, septicaemia and pneumonia, and the prevention and treatment of these diseases is especially preferred in the present invention. Diseases caused by *Neisseria gonorrhoeae* include sexually transmitted diseases such as urethritis, cervicitis, proctitis pharyngitis, salpingitis, epididymitis and bacteremia/arthritis. Additionally, the invention extends to treatment and prevention of any other disease which results from *Neisseria* infection, especially to diseases in which *Neisseria* infection could weaken the immune system such that another disease or pathogen could be harmful to an individual. The treatment can be preventative or curative.

The vaccine of the present invention is a formulation suitable for safe delivery to a subject, allowing the subject to develop an immune response to future infection by *Neisseria*. Vaccines of the present invention are preferably formulated vaccines in which any of the immunogenic components of the vaccine may be conjugated, and any suitable agent for conjugation may be used. Conjugation enables modification of the presentation of the antigen, and may be achieved by conventional techniques. Examples of agents for conjugation include proteins from homologous or heterologous species. In this way, the immunogenic component of the present invention forms a saccharide peptide conjugate. Preferably the peptide portion comprises a T cell activating epitope.

The vaccines of the present invention may be delivered with an adjuvant, to enhance the immune response to the immunogenic components. Suitable adjuvants include aluminium salts, oils in combination with bacterial macromolecules, liposomes, muramyl dipeptide, ISCOMS, bacterial toxins such as pertussis, cholera and those derived from *E. coli* and cytokines such as IL-1, IL-2 and IFNγ.

The vaccine of the invention may be delivered by suitable means, such as by oral delivery or parenteral administration, injection, nutraceutical or other delivery means, and may be provided in any suitable delivery form such as tablets, pills, capsules granules, solutions, suspensions or emulsions. Suitably the vaccine components are prepared in the form of a sterile, isotonic solution.

The present invention also extends to the monoclonal antibodies derived from the concepts and methodologies described herein, including but not limited to B5 and A4, and use of these antibodies in the treatment of *Neisseria* infection. The invention also relates to pharmaceutical preparations comprising such antibodies in combination with pharmaceutically acceptable carrier. Such preparations may be delivered by any suitable means, such as those exemplified above for vaccine delivery, and used in combination with other active agents or adjuvants.

The correct dosage of the antibody or vaccine will vary according to the particular formulation, mode of application, and the particular host being treated. Factors such as age, body weight, sex, diet, and time of administration, rate of excretion, condition of the host, drug combinations, and reaction sensitivities are suitably to be taken into account.

The antibodies and vaccine compositions of the present invention may be used with other drugs to provide combination treatments. The other drugs may form part of the same composition, or be provided as a separate composition for administration at the same time or a different time.

In addition to the antibodies themselves, the invention also relates to the hybridomas which produce such antibodies.

Antibodies against the immunogenic components of the invention may be generated by administering the immunogenic components to an animal, preferably a non-human animal using standard protocols. For the preparation of monoclonal antibodies, any suitable techniques can be used. Techniques for the production of single chain antibodies (U.S. Pat. No. 4,946,778) can be adapted to produce appropriate single chain antibodies. Moreover, transgenic mice or other organisms or animal may be used to express humanized antibodies immunospecific to the immunogenic components of the invention.

Alternatively, other methods, for example phage display technology may be used to select antibody genes for proteins with binding activities towards immunogenic components of the present invention.

Antibodies of the invention may be either monoclonal or polyclonal antibodies, as appropriate.

The present invention also relates to a method for the prevention of *Neisseria* infection, the method comprising administering to a subject in need of such treatment an effective amount of a vaccine as described above. Preferably the administration is adequate to produce a long lasting antibody and/or T cell immune response to protect the subject from infection, particularly *Neisseria meningitidis* infection.

The invention also relates to a method for the treatment of *Neisseria* infection, the method comprising administering to a subject in need of such treatment an effective amount of an antibody to the *Neisseria meningitidis* inner core. Preferably, the antibody is B5 or A4, or an antibody which recognizes the same epitope as B5 or A4, or an antibody derived from the concepts and methodologies herein described, or is a combination thereof.

Moreover, the methods of the invention may be extended to identification of epitopes in any bacterial strain. Epitopes so identified may be tested both for accessibility, conservation across the population and functional activity, using methods as outlined in the attached Examples. The present invention thus additionally relates to a method for the identification of an immunogenic element, comprising raising an antibody to a bacterial structure, preferably bacterial LPS structure, more preferably a bacterial inner core LPS structure, and testing the epitope recognized by the antibody for accessibility to antibody in the wild type strain optionally also comprising testing the epitope for conservation across the bacterial population and testing for functional activity to the epitope in vivo.

Preferably the bacterial species are *Neisseria* species, preferably *Neisseria meningitidis*,

*Neisseria gonorrhoeae* or *Neisseria lactamica.*

Specifically, the present invention provides a method to generate antibodies to the inner core of *Neisseria meningitidis*. For the first time it has been possible to screen a population of *Neisseria meningitidis* strains to identify whole population features which are independent of immunotype.

Accordingly, the present invention also relates to a method for the identification of immunogenic epitopes of *Neisseria meningitidis*, the method comprising the steps of:

1. generating antibodies to the inner core of *Neisseria meningitidis*, by inoculation of host organism with a galE mutant strain of *Neisseria meningitidis*, and 2. testing such antibodies against a wild type *Neisseria meningitidis* strain to identify those antibodies which are reactive, and for which the epitopes are therefore accessible.

The potential utility of epitopes so identified may be further assessed by screening antibodies which react with the inner core of *Neisseria meningitidis* galE strain against a panel of strains which are representative of strain diversity. Preferably the strain panel is selected using an approach based upon a population analysis. Epitopes so identified may then be tested in functional assays, as outlined in Example 3.

In particular the invention extends to a method for the analysis of antibody binding to bacteria wherein natural isolates of bacteria are studied when grown on and adherent to tissue cultured cells, such as HUVECs. This assay provides a monolayer of cells to which the bacteria adhere in a biologically relevant environment. Previous attempts using *Neisseria*, for example, directly adherent to gelatin- or MATRIGEL-coated coverslips resulted in low numbers of adherent bacteria after repeated washings and high non-specific background staining. In particular we prefer that the antibody binding is analyzed using confocal microscopy.

This method also identifies antibodies suitable for therapeutic use, and the invention extends to such antibodies.

Moreover, key biosynthetic genes for each step in LPS synthesis have been identified (Preston et al., 1996. Crit. Rev. Microbiol. 22: 139-180) and this allows the construction of a series of mutants from which LPS glycoforms of varying size and complexities can be made available to facilitate the identification of conserved epitopes (van der Ley et al., 1997. FEMS Microbiol. Letter 146: 247-253; Jennings et al., 1993, Mol. Microbiol. 361-369; Jennings et al., 1995. Microb. Pathog. 19: 391-407; van der Ley et al., 1996, Mol. Microbiol. 19: 1117-1125).

The present invention also relates to the gene found in *Neisseria meningitidis* which is involved in PEtn substitution at the 3-position on HepII, and to genes related in structure and function. As yet no genes have been identified in any bacteria that are involved in addition of PEtn to LPS structures. Using B5, specific for an inner core LPS epitope containing a PEtn, we have identified a putative LPS phosphoethanolamine transferase gene (designated hypo3) in *Neisseria meningitidis*. Hypo3 was named arbitrarily by us, as it is the 3rd reading frame in a fragment of DNA selected by experimentation, from the MC58 genome sequence. The original hypo3 is therefore from MC58. This ORF is called NMB2010 in the TIGR data base (MC58 genome sequence) and although designated as a protein of unknown function, they classify it as a "YhbX/YhjW/YjP/YjdB family protein". This indicates that homologues have been inferred in other organisms but they do not know the function of them. The homologue in the serogroup A sequence at the Sanger Centre is designated NMA0431, although this gene is smaller than hypo3. Hypo3 is involved in PEtn substitution at the 3-position at HepII. Furthermore, the presence of the complete gene is required for the expression of the B5 reactive phenotype in *Neisseria meningitidis* as well as other pathogenic and commensal *Neisseria* species.

The identification of the gene allows mutants to be created which are isogenic apart from hypo3, and which differ only in the presence or absence of PEtn at the 3-position of HepII in the LPS inner core. Such strains can be used in comparative studies. Moreover, strains appropriate for vaccine production can be engineered so that they comprise the preferred PEtn structure at the 3-position, or engineered so that this PEtn cannot be present.

Accordingly, the invention relates to use of the hypo3 gene, or homologue thereof, in the production of a *Neisseria* strain for the assessment, treatment or prevention of *Neisseria* infection. The homologue may have 60%, 70%, 80%, 90% or more homology or identity to hypo3, as assessed at the DNA level. Use of the gene includes the methods outlined above, for preparing genetically modified strains for vaccination, isolation of appropriate epitopes and generation of strains for comparative studies. More generally, we envisage the identification and use of any gene which plays a role in the biosynthetic pathway, and which has an effect on the conservation, accessibility or function of the immunogen.

EXAMPLES

Example 1

Identification of Immunogenic Epitopes in *Neisseria meningitidis*

Introduction

We investigated the conservation and antibody accessibility of inner core epitopes of *Neisseria meningitidis* lipopolysaccharide (LPS) because of their potential as vaccine candidates. An IgG3 murine monoclonal antibody (MAb), designated MAb B5, was obtained by immunizing mice with a galE mutant of *Neisseria meningitidis* H44/76 (B.15.P.1.7.16 immunotype L3). We have shown that MAb B5 can bind to the core LPS of wild-type encapsulated MC58 (B.15.PI.7.16 immunotype L3) organisms in vitro and ex-vivo. An inner core structure recognized by MAb B5 is conserved and accessible in 26/34 (76%) of Group B and 78/112 (70%) of Groups A, C, W, X, Y, and Z strains. *Neisseria meningitidis* strains which possess this epitope are immunotypes in which phosphoethanolamine (PEtn) is linked to the 3-position of the β-chain heptose (HepII) of the inner core. In contrast, *Neisseria meningitidis* strains lacking reactivity with MAb B5 have an alternative core structure in which PEtn is linked to an exocyclic position (i.e. position 6 or 7) of HepII (immunotypes L2, L4 and L6) or is absent (immunotype L5). We conclude that MAb B5 defines one or more of the major inner core glycoforms of *Neisseria meningitidis* LPS.

These findings encourage the possibility that immunogens capable of eliciting functional antibodies specific to inner core structures could be the basis of a vaccine against invasive infections caused by *Neisseria meningitidis*.

Figure 1B:
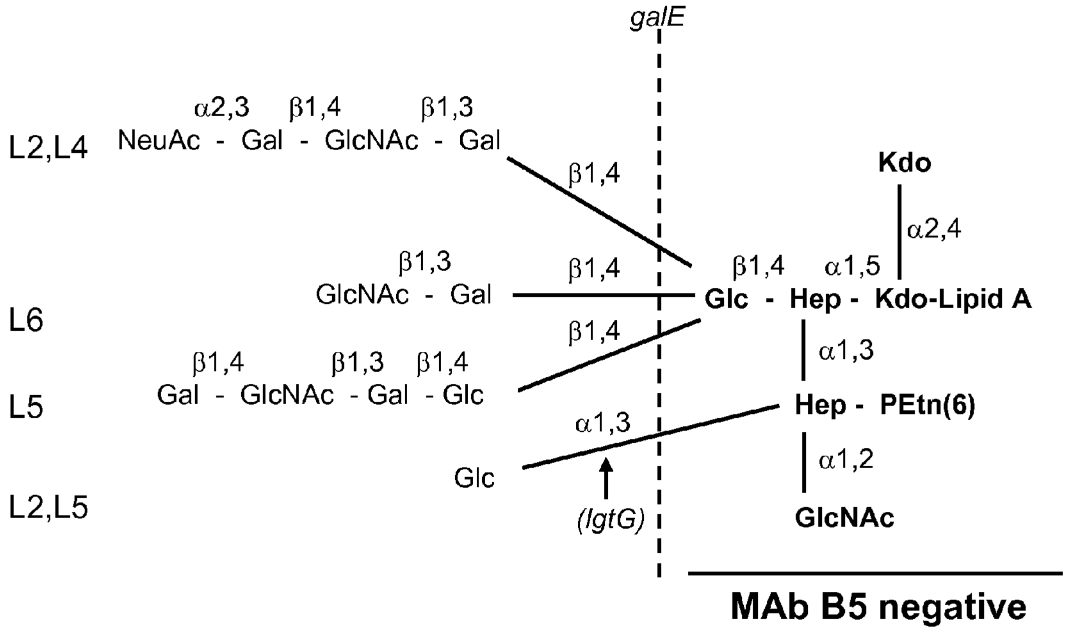

In summary, we report that a monoclonal antibody, designated B5, has identified a cross-reacting epitope on the LPS of the majority of naturally occurring, but genetically diverse strains of *Neisseria meningitidis*. Critical to the epitope of strains recognized by the monoclonal antibody B5 is a phosphoethanolamine (PEtn) on the 3-position of the β-chain heptose (HepII) (FIG. 1A). In contrast, all *Neisseria meningitidis* strains lacking reactivity with MAb B5 are immunotypes characterized by the absence of PEtn substitution or by PEtn substitution at an exocyclic position (i.e. position 6 or 7) of HepII (FIG. 1B). Thus, a limited repertoire of inner core LPS variants is found among natural isolates of *Neisseria meningitidis* strains and these findings encourage the possibility that a vaccine might be developed containing a few glycoforms representative of all natural *Neisseria meningitidis* strains.

Materials and Methods

Bacterial Strains

The *Neisseria meningitidis* strains MC58 and H44/76 (both P:15:P1.7.16 immunotype L3) have been described previously (Virji, M., et al., 1991. Mol. Microbiol. 5: 1831-1841; Holten, E. 1979. J. Clin. Microbiol. 9: 186-188). Derivatives of MC58 and H44/76 with defined alterations in LPS were obtained by inactivating the genes, galE (Jennings, M. P., et al., 1993. Mol. Microbiol. 10: 361-369), lsi (Jennings, M. P., et al., 1995. Microb. Pathog. 19: 391-407), IgtA, IgtB (Jennings, M. P., et al., 1995. Mol. Microbiol. 18: 729-740), rfaC (Stoiljkovic, I., et al., 1997. FEMS Microbiol Lett. 151: 41-49), icsA and icsB (van der Ley, P., et al., 1997. FEMS Microbiol. Lett. 146: 247-253) (Table 1). Other wild type *Neisseria meningitidis* strains used in the study were from three collections: 1) representatives of immunotypes L1-L12 (Poolman, J. T., et al., FEMS Microbiol Lett. 13: 339-348); 2) global collection of 34 representative *Neisseria meningitidis* Group B strains (Seiler, A., et al., 1996. Mol. Microbiol. 19: 841-856); 3) global collection of 100 strains from 107 representative *Neisseria meningitidis* strains of all major serogroups (A, B, C, W, X, Y, Z) (Maiden, M. C. J., et al., 1998 PNAS 95: 3140-3145).

Capsule deficient and galE mutants were constructed in six *Neisseria meningitidis* Group B strains obtained from the collection as described in (Seiler, A., et al., 1996. Mol. Microbiol. 19: 841-856) (Table 1). Other related *Neisseria* strains studied included 10 strains of *Neisseria gonorrhoeae* and commensal strains lactamica (8 strains), polysaccharea (1 strain), mucosa (1 strain), cinerea (1 strain), elongata (1 strain), sicca (1 strain) and subflava (1 strain). Other Gram negative organisms included: *Haemophilus influenzae* type b (7 strains), *Haemophilus somnus* (1 strain), non-typable *Haemophilus influenzae* (8 strains), *Escherichia coli* (1 main) and *Salmonella typhimurium* (1 strain) and its isogenic LPS mutants (rfaC, rfaP, and rfal) (Table 1).

Bacterial Culture In Vitro

All strains were grown overnight at 37° C. on standard BHI medium base (Oxoid) in an atmosphere of 5% $CO_2$ Bacterial Culture In Vivo Using the Chick Embryo Model To determine the accessibility of inner core epitopes of *Neisseria meningitidis* grown in vivo the chick embryo model was used (Buddingh, G. J., and A. Polk. 1937. Science 86: 20-21; Buddingh, G. J., and A. Polk. 1939. J. Exp. Med. 70: 485-498; Schroten, H., et al., 1995. Pediar. Grenzgeb. 34: 319-324). The method was modified using an inoculum of $10^4$ and $10^5$ *Neisseria meningitidis* organisms in a final volume of 0.1 ml, to infect the chorio-allantoic fluid of 10 day old Pure Sussex chick eggs (obtained from the Poultry Unit Institute of Animal Health, Compton, Berks). After overnight incubation (37° C.) the allantoic fluid (approx. 3-5 mls) was removed from the eggs and the bacteria recovered after centrifugation at 350×g for 15 minutes. The organisms were washed in sterile phosphate buffered saline (PBS) and stored in Greaves solution (5% BSA, 5% Sodium Glutamate, 10% Glycerol) at −70° C.

LPS Extraction

LPS samples were obtained from an overnight growth of *Neisseria meningitidis* plated on 5 BHI plates from which the organisms were scraped and suspended in 30 ml 0.05% phenol in PBS and incubated at room temperature for 30 minutes. Alternatively, batch cultures were prepared in fermenters using bacteria from an overnight growth (6 plates) in 50 ml DIFCO BACTO Todd Hewitt broth (DIFCO) to inoculate 2.5 L of the same medium. For insertion mutant strains; the medium contained 50 μg/ml kanamycin. Following incubation at 37° C. for 6-8 h the culture was inoculated into 60 L of BACTO Todd Hewitt broth in a New Brunswick Scientific 1F-75 fermenter. After overnight growth (I7h at 37° C.), the culture was killed by addition of phenol (1%), and chilled to 15° C. and the bacteria were harvested by centrifugation (13,000 g for 20 min) (Wakarchuk W., et al., 1996. J. Biol. Chem. 271: 19166-19173). In either case, the crude LPS were extracted from the bacterial pellet using the standard hot phenol-water method (Westphal, O., and J. K. Jann. 1965. Meth. Carbohydr. Chem. 5: 83-91) and purified from the aqueous phase by repeated ultracentrifugation (105,000×g, 4° C., 2×5 h) (Masoud, H., et al., 1997. Biochemistry 36: 2091-2103).

Tricine Gels

Equivalent amounts of whole-cell lysates of. *Neisseria meningitidis* strains or purified LPS were boiled in dissociation buffer and separated on standard tricine gels (30 mA for 18 h) (Lesse, A. J., et al., 1990. J. Immunol. Methods. 126: 109-117). Gels were fixed and silver-stained as per manufacturer's instructions (BioRad). To determine the presence of sialic acid, whole cell lysates were incubated with 2.5 μl neuraminidase at 37° C. for 18-20 h (4 U/ml Boehringer 1585886) and then with 5 μl proteinase K at 60° C. for 2-3 h to remove proteins (Boehringer 1373196) prior to separation on tricine gels (16.5%).

Characterization of LPS from MAb 85 Negative Strains

LPS from wild-type and galE, cap- mutant MAb B5 negative strains were O-deacylated with anhydrous hydrazine as described previously (Masoud, H., et al., 1997. Biochemistry 36: 2091-2103). O-deacylated LPS was analyzed by electrospray mass spectrometry (ES-MS) in the negative ion mode on a VG Quattro (Fisons Instruments) or API 300 (Perkin-Elmer/Sciex) triple quadruple mass spectrometer. Samples were dissolved in water which was diluted by 50% with acetonitrile: water:methanol: 1% ammonia (4:4:1:1) and the mixture was enhanced by direct infusion at 4 μl/min. Deacylated and dephosphorylated LPS (L8 odA HF) was prepared according to the following procedure. LPS (160 mg) was treated with anhydrous hydrazine (1.5 ml) with stirring at 37° C. for 30 minutes. The reaction was cooled (0° C.), cold acetone (−70° C., 50 ml) was added gradually to destroy excess hydrazine, and precipitated O-deacylated LPS (L8 odA) was obtained by centrifugation. L8 odA was washed twice with cold acetone, and redissolved in water and lyophilized. The structure of L8 odA was confirmed by negative ion ES-MS before proceeding to dephosphorylation. L8 odA was dephosphorylated by treatment with 48% aqueous hydrogen fluoride (10 ml) at 0° C. for 48 h. The product was dialyzed against water, and the O-deacylated, dephosphorylated LPS sample (L8 odA HF) was lyophilized (50 mg). Loss of phosphate was confirmed by ES-MS.

Molecular Modeling

Molecular modeling of LPS epitopes was carried out as described previously by Brisson, J. R., S. et al., 1997. Biochemistry 36: 3278-3292). The starting geometry for all sugars was submitted to a complete refinement of bond lengths, valence and torsion angles by using the molecular mechanics program MM3(92) (QPCE). All calculations were performed using the minimized co-ordinates for the methyl glycoside. The phosphorus groups were generated from standard coordinates (ALCHEMY, Tripos software) and minimum energy conformations found in crystal structures. Calculations were performed using the Metropolis Monte Carlo (MMC) method. All pendant groups were treated as invariant except for the phosphorus groups which were allowed to rotate about the Cx-Ox and Ox-P bonds. The starting angles for the oligosaccharide were taken from the minimum energy conformers calculated for each disaccharide unit present in the molecule. 24-dimensional MMC calculations of the hexasaccharides with or without PEtn groups attached were carried out with 5000 macro moves. The graphics were generated using the Schakal software (Egbert Keller, KristallographischesInstitut der Universitat, Freibury, Germany).

Antibodies

Rabbit Polyclonal Antibody

We used a rabbit polyclonal antibody specific for Group B *Neisseria meningitidis* capsular polysaccharide obtained by immunizing a rabbit six times sub-cutaneously with lysates of MC58 at 2-week intervals. The first and second immunizations contained Freund's complete adjuvant and Freund's incomplete adjuvant respectively. Serum was obtained from bleed 6. To increase specificity for the Group B capsular polysaccharide, rabbit polyclonal antibody (1 ml) was incubated overnight at 4° C. with ethanol-fixed capsule-deficient MC58 ($5\times10^9$ org./ml). This pre-adsorbed polyclonal antibody did not react with a capsule-deficient mutant of MC58 using immunofluorescence microscopy.

Monoclonal Antibodies to Inner Core LPS

Murine monoclonal antibodies to H44/76 galE LPS were prepared by standard methods. Briefly, 6-8 week old Balb/c mice were immunized three times intraperitoneally followed by one intravenous injection with formalin-killed galE mutant whole cells. Hybridomas were prepared by fusion of spleen cells with SP2/O-Ag 14 (Shulman, M., et al., 1978. Nature 276: 269-270) as described (Carlin, N. I., et al., 1986. J. Immunol. 137: 2361-2366). Putative hybridomas secreting galE specific antibodies were selected by ELISA employing purified LPS from L3 and its galE mutant, and L2. Ig class, subclass and light chain were determined by using an isotyping kit (Amersham Canada Ltd, Oakville, Ontario). Clones were expanded in Balb/c mice following treatment with pristane to generate ascitic fluid. Spent culture supernatant was collected following in vitro culture of hybridoma cell lines. Further testing of galE MAbs was, carried out by screening against purified LPS from *Neisseria meningitidis* L3 IgtA, IgtB, and IgtE mutant strains (FIG. 1A), and *Salmonella typhimurium* Ra and Re mutants. One of the MAbs, MAb B5 ($IgG_3$), was selected for more detailed study.

Immunotyping Monoclonal Antibodies

To determine the immunotypes of *Neisseria meningitidis* strains studies, especially L2 and L4-L6, the following murine MAbs were used in dot blots and whole cell ELISA: MN42F12.32 (L2,5), MN4A8B2 (L3,7,9), MN4C1B (L4,6, 9), MN40G11.7 (L6), MN3A8C (L5) (Scholten, R. J., et al., J. Med. Microbial. 41: 236-243).

Human Umbilical Vein Endothelial Cell (HUVEC) Assay

Cultured human umbilical vein endothelial cells (HUVECs) were prepared as described previously (Virji, M., et al., 1991. Microb. Pathog. 10: 231-245) and were infected with strains of *Neisseria meningitidis* for 3 h at 37° C. *Neisseria meningitidis* strains were grown either in vitro or in vivo using the chick embryo model (as described above). The accessibility of the inner core LPS epitopes of whole-cell *Neisseria meningitidis* to specific MAb B5 was determined using immunofluorescence and confocal microscopy. Gelatin-coated glass coverslips coated with HUVECs were infected with wild-type *Neisseria meningitidis* as described previously (Virji, M., et al., 1991. Mol. Microbial. 5: 1831-1841), except bacteria were fixed with 0.5% paraformaldehyde for 20 min instead of methanol. For accessibility studies, coverslips were washed with PBS, blocked in 3% BSA-PBS and incubated with MAb B5 culture supernatant and pre-adsorbed polyclonal rabbit anti-capsular antibody. Binding of antibody to wild-type *Neisseria meningitidis* strains was detected by anti-mouse IgG rhodamine (TRITC) (Dako) and anti-rabbit IgG fluorescein (FITC) (Sigma). HUVECs were stained using diaminophenylamine DAPI (1 μg/ml) (Sigma). Mounted coverslips were viewed for immunofluorescence using appropriate filters (Zeiss Microscope with Fluorograbber, Adobe Photoshop or confocal microscope (Nikon Model).

ELISA

Purified LPS ELISA

A solid phase indirect ELISA employing purified LPS was used to determine the binding specificities of MAbs. NUNC MAXISORP plates were coated overnight with 1.0 μg/well of purified LPS derived from wild type and mutants. LPS (10 μg/ml) was diluted in 0.05M carbonate buffer containing 0.02M $MgCl_2$, pH 9.8. Non-specific binding sites were blocked for 1 h with 1% BSA-PBS (Sigma) and washed three times with PBS-TWEEN 20 (0.05% v/v) (PBS-T). Plates were incubated for 1 h with MAb B5 culture supernatant and washed three times in PBS-T. Primary antibody was detected using anti-mouse IgG-alkaline phosphatase (Sigma: Cedarlane Laboratories Ltd.) incubated for 1 h, washed three times in PBS-T, and detected using p-nitrophenyl phosphate AP substrate system (Sigma: Kirkegaard & Perry Laboratories). The reaction was stopped after 1 h with 50 μl 3M NaOH and absorbance determined at OD $A_{405-410\ nm}$ (Dynatech EIA plate reader).

Inhibition ELISA

For inhibition ELISA studies, MAb B5 was incubated with purified LPS samples prior to addition to L3 galE LPS coated plates and assayed as described above.

Whole Cell ELISA

Whole cell (WC) ELISA was performed using heat-inactivated lysates of *Neisseria meningitidis* organisms as described previously (Abdillahi, H., and J. T. Poolman. 1988. J. Med. Microbial. 26: 177-180). NUNC MAXISORP 96-well plates were coated with 100 μl bacterial suspension (OD of 0.1 at $A_{820\ nm}$) overnight at 37° C., blocked with 1% BSA-PBS and identical protocol followed as for LPS ELISA.

Dot Blots

Bacterial suspensions prepared as above (2 μl) were applied to a nitrocellulose filter (45 micron, Schleicher and Schueller) and allowed to air dry. The same procedure as described for WC ELISA was followed except the detection substrate was 5-bromo-4-chloro-3-indoyl phosphate/nitroblue-tetrazolium (BCIP/NBT) (2 mg/ml; Sigma). The color reaction was stopped after 30 min by several washes with PBS and blots were air-dried.

Results

To investigate the potential of inner core LPS structures of *Neisseria meningitidis* as vaccines, we have studied the reactivity of an isotype $IgG_3$ murine monoclonal antibody (MAb), designated B5, raised against *Neisseria meningitidis* stain H44/76 immunotype L3 galE mutant. MAb B5 was one of seven monoclonal antibodies to LPS inner core produced against *Neisseria meningitidis* immunotype L3 galE by standard immunological methods (see Methods). Preliminary ELISA testing showed B5 cross-reacted with LPS from L3 parent strain and with galE (lgtE), IgtA and lgtB mutants, but did not cross-react with *Salmonella typhimurium* Ra or Re LPS.

Figure 2:
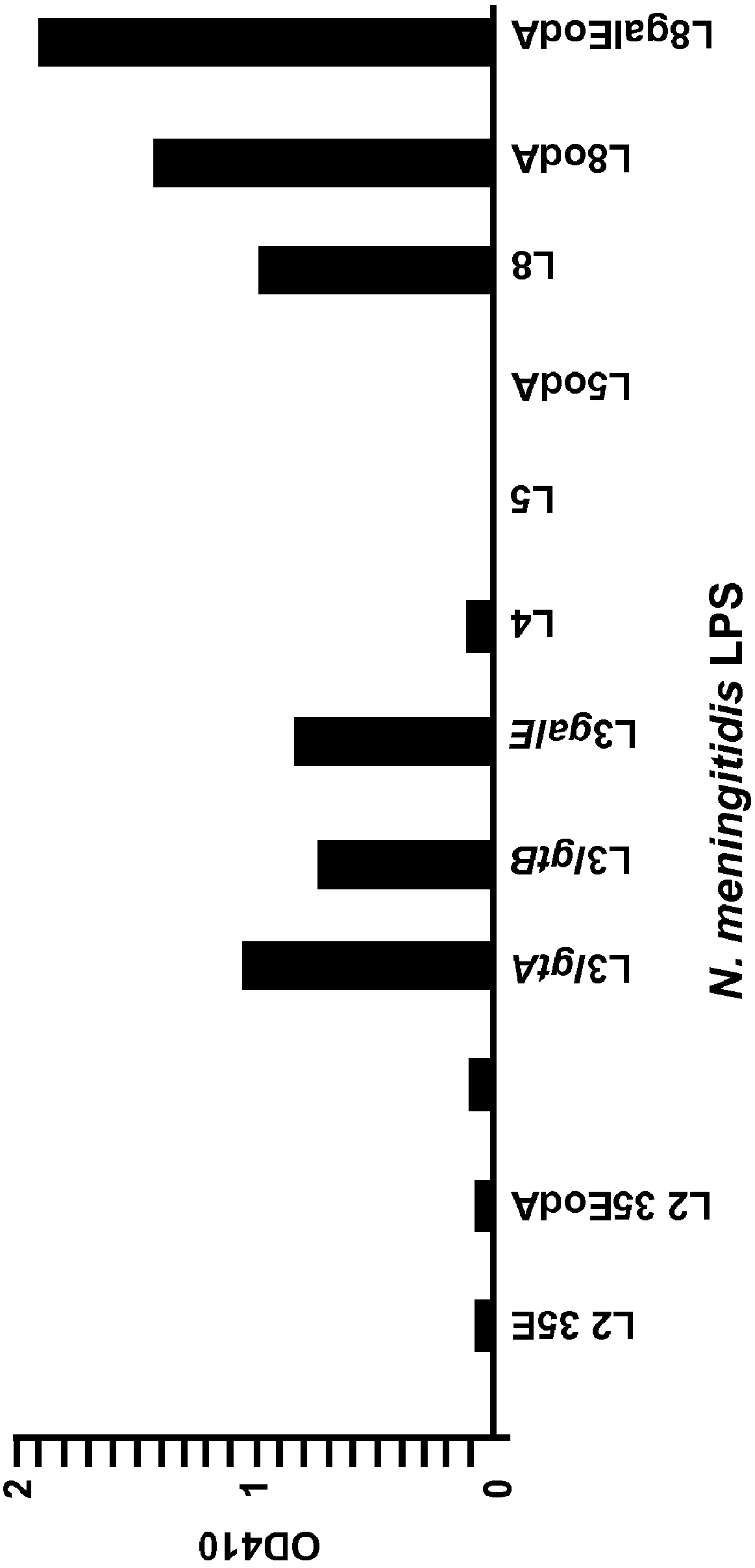
FIG. 2 illustrates cross reactivity of monoclonal antibody B5 with selected immunotypes and mutants of *Neisseria meningitidis* LPS. Cross-reactivity of MAb B5 with selected immunotypes and mutants of *Neisseria meningitidis* LPS and O-deacylated (odA) LPS was determined by solid phase ELISA. LPS glycoforms of immunotypes L2 (35E), L3 (H44/76), L4 (891), L5 (M981), L8 (M978), wild-type and respective mutants (galE, IgtA or IgtB), in a native or O-deacylated form, were coated onto ELISA plates (see methods) and reactivity of MAb B5 determined by standard ELISA (OD $A_{450}$).

In order to determine the specific inner core epitope recognized by MAb B5, various *Neisseria meningitidis* strains of known structure were examined in ELISA for cross reactivity (FIG. 2). The most significant finding of this analysis was that *Neisseria meningitidis* immunotype L4 LPS was not recognized by MAb B5. The only structural difference between immunotypes L4 and L3 (which is recognized by MAb B5) is the position of attachment of the PEtn group (FIGS. 3A-3C). In immunotype L3 LPS the PEtn is attached at the 3-position of HepII, whereas in immunotype L4 LPS the PEtn is attached at the 6- or 7-position of HepII (FIGS. 3A and 3B). Additionally, LPS from immunotype L2 and its galE mutant (in which the PEtn group is attached at the 6-position and a glucose residue is present at the 3-position of HepII) are not recognized by MAb B5. Immunotype L5, which has no PEtn in the inner core, is not recognized by B5, whereas immunotype L8 and its galE mutant which have PEtn at the 3-position of HepII are recognized. These results suggest that MAb B5 specifically recognizes PEtn when it is attached at the 3-position of HepII.

Figure 4:
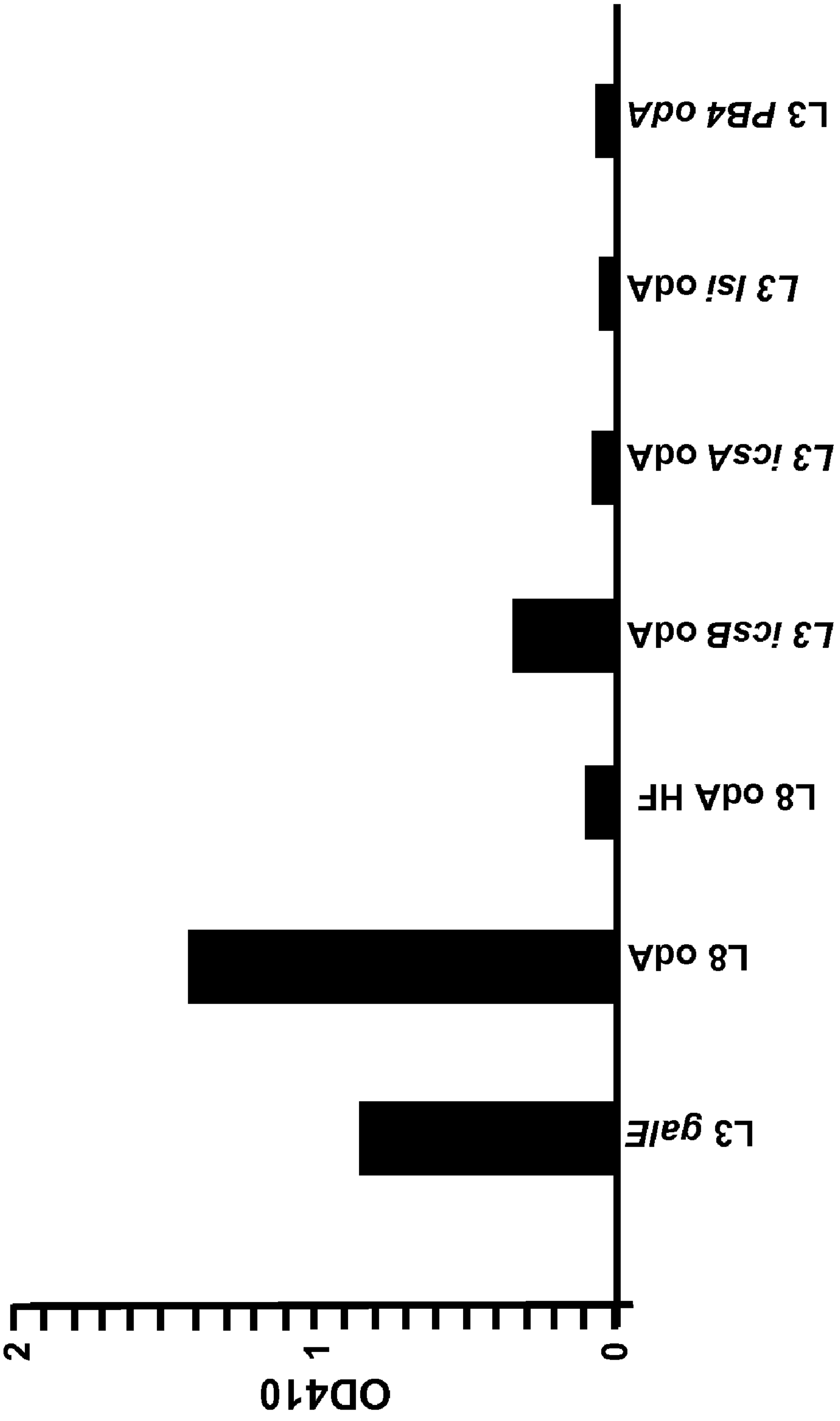
FIG. 4 illustrates cross reactivity of B5 with genetically modified L3 LPS and chemically modified L8 LPS from *Neisseria meningitidis* as determined by solid phase ELISA. LPS glycoforms of immunotype L8 (M978) chemically modified by O-deacylation and HF treatment and immunotype L3H44/76) galE, icsB, icsA, lis;. PB4 mutants (O-deacylated) were coated onto ELISA plates (see methods) and reactivity of MAb B5 determined by standard ELISA ($OD_{4410\ nm}$).

In order to prove the essential inclusion of PEtn in the epitope recognized by MAb B5, immunotype L8 O-deacylated (odA) LPS was dephosphorylated (48% HF, 4° C. 48 h) (FIG. 3C). The absence of PEtn following dephosphorylation was confirmed by ES-MS analysis. As indicated in FIG. 4, dephosphorylation of L8 odA LPS abolished reactivity to MAb B5. To further characterize the epitope recognized by MAb B5, several structurally defined genetic mutants of immunotype L3 were screened for cross-reactivity (FIG. 4). The highly truncated LPS of mutant strain icsB were only weakly recognized, while mutant strain icsA LPS was not recognized by MAb B5. These results suggest that the presence of glucose on the proximal heptose reside (HepI) is not absolutely necessary for binding by B5 but is required for optimal recognition (FIG. 1A). Furthermore, MAb B5 does not bind LPS in which both the glucose on the α-chain, HepI, and the N-acetylglucosamine residue on the β-chain, HepII, are absent. This suggests that the presence of N-acetylglucosamine is required to present the PEtn residue in the correct conformation for binding by MAb B5. Genetic modifications that produce severely truncated LPS glycoforms were also examined for reactivity with MAb B5. LPS from immunotype L3 Isi which has a trisaccharide of Hep-Kdo-Kdo attached to lipid A, and L3 PB4 which only contains the Kdo disaccharide and lipid A were not recognized by MAb B5 (FIG. 4). Inhibition ELISA studies (data not shown) were in accord with this result, thus confirming the specificity of MAb B5 to the PEtn molecule linked at the 3-position of HepII.

To demonstrate the ability of MAb B5 to recognize this inner core epitope in encapsulated strains, we devised an assay in which natural isolates of *Neisseria meningitidis* were studied when they were grown on and became adherent to tissue cultured cells (HUVECs). Initially, this methodology was developed using the fully encapsulated strain MC58. The advantages of using the HUVEC assay were that they provided a monolayer of endothelial cells to which the bacteria could adhere and that they provided a biologically relevant environment. Previous attempts using *Neisseria meningitidis* directly adherent to gelatin- or MATRIGEL-coated coverslips resulted in low numbers of adherent bacteria after repeated washings and high nonspecific background staining.

Figure 5A:
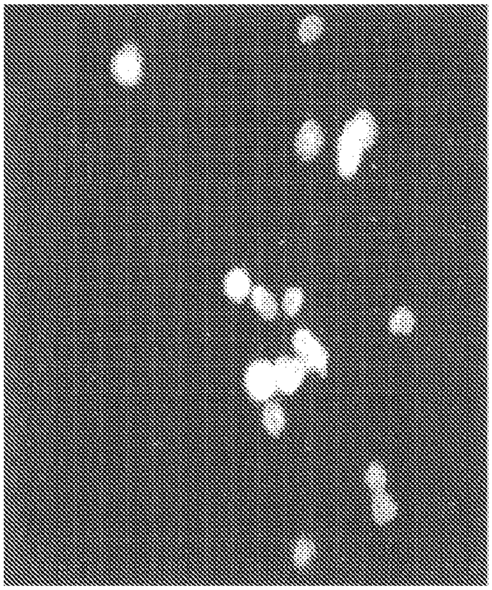
FIGS. 5A-5D illustrate confocal immunofluorescence microscopy of *Neisseria meningitidis* organisms strain MC58 adherent to HUVECs. Confocal immunofluorescence microscopy of *Neisseria meningitidis* organisms, strain MC58 adherent to human umbilical vein endothelial cells (HUVECs).
Figure 5B:
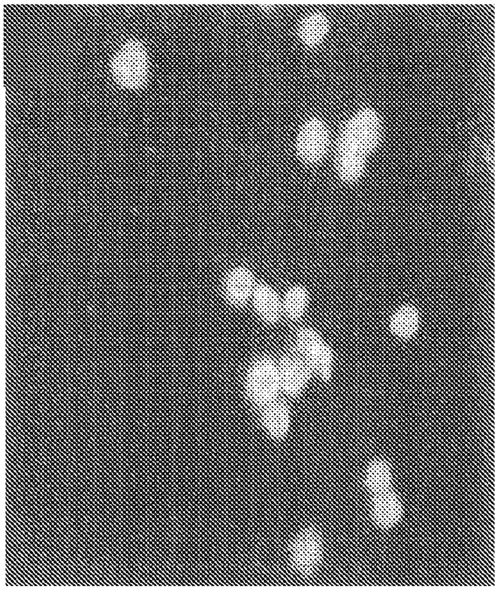
Figure 5C:
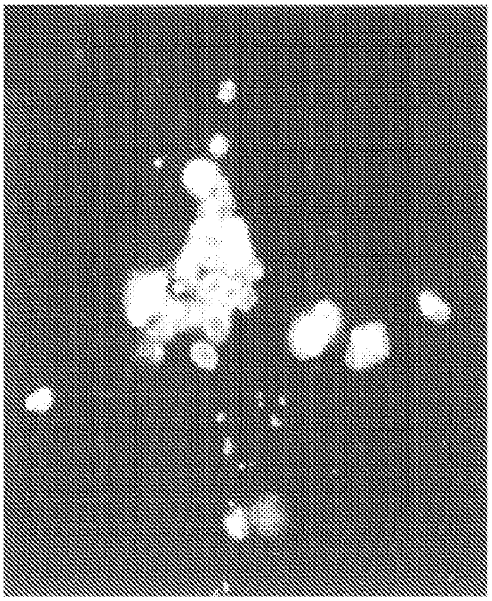
Figure 5D:
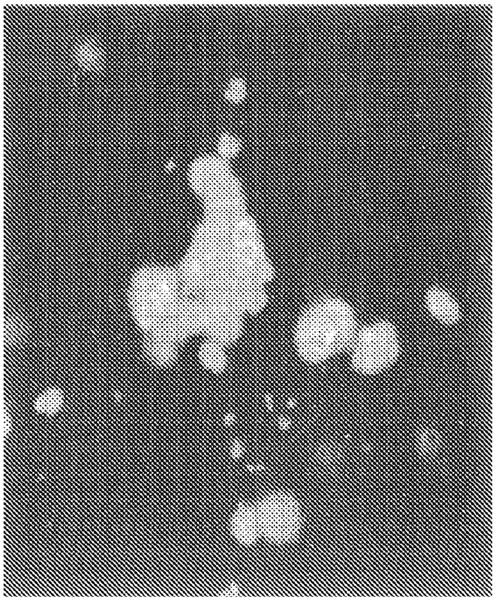

Primary antibodies, MAb B5 and a polyclonal anti-capsular antibody were detected by anti-mouse TRITC and anti-rabbit FITC respectively. This demonstrated that an inner core LPS epitope of the fully encapsulated strain (MC58) was accessible to MAb B5 (FIG. 5A). Confocal microscopy showed that MAb B5 and anti-capsular antibodies co-localized. In addition to this in vitro demonstration of accessibility of MAb B5 to inner core LPS, we also investigated organisms grown in vivo using the chick embryo model. Strain MC58 ($10^4$ org./ml) was inoculated into chorioallantoic fluid of 10 day old chick embryos and harvested the next day to provide ex-vivo organisms. The results of confocal microscopy were identical to those observed in vitro, that is MAb B5 and anti-capsular antibodies co-localized (FIG. 5B). This demonstrated that the inner core LPS epitopes were also accessible in vivo on whole-encapsulated wild-type *Neisseria meningitidis*.

The observation of double staining of the inner core LPS epitope in the presence of capsule is key to the concept of this approach and therefore a number of controls were used to confirm the validity finding. These included: (i) double staining a MAb B5 negative e.g. immunotype L4 strain with MAb B5 and anti-capsular antibody. This resulted in no reactivity of MAb B5 on rhodamine filter but positive reactivity with anti-capsular antibody. This rules out a band passing effect during the recording of the pictures; (ii) single staining of encapsulated MAbB5 positive strains with either MAb B5 alone or anti-capsular antibody alone followed by staining with rhodamine or FITC, respectively. When viewed on the appropriate wavelength there was no cross-reactivity during immunofluorescent staining nor any band-passing effect; (iii) double-staining of a MAb B5 positive or negative strain without capsule with MAb B5 and anti-capsular antibody resulted in no capsular staining but either MAb B5 positive or negative reactivity when viewed on the rhodamine filter. This excluded cross-reactivity during staining or band-passing effect resulting in artefactual inner core staining.

To survey the extent of MAb B5 reactivity with other *Neisseria meningitidis* strains, three collections were investigated.

i) 12 strains representative of LPS immunotypes L1-L12 ii) 34 Group B strains selected to represent genetically diverse isolates from many different countries obtained between the years 1940-1988 (Seiler, A., et al., 1996. Mol. Microbiol. 19: 841-856)

iii) a global collection of 107 genetically diverse strains representing all capsular serogroups, also obtained from different countries from 1940-1994 (Maiden, M. C. J., et al., 1998. PNAS 95: 3140-3145).

Of the 12 immunotypes, MAb B5 recognized the LPS of strains in which the inner core oligosaccharide has a PEtn linked to the 3-position of HepII (Table 2 and FIG. 1A). Thus, immunotypes L2, L4, L6 did not react with MAb B5, whereas immunotypes L1, L3, L7-L12 were recognized by MAb B5. This confirmed that the presence of PEtn in the 3 position of the HepII is necessary to confer MAb B5 reactivity (FIG. 3A).

To investigate further the MAb B5 reactivity with other Group B strains, a collection of genetically diverse strains was studied (Seiler, A., et al., 1996. Mol. Microbiol. 19: 841-856). MAb B5 reactivity was detected in 26/34 (76%) of Group B *Neisseria meningitidis* stains tested. This included representative strains of ET-5, ET-37, A4 and Lineage-3. This represents the most complete available collection of hyper-invasive lineages of *Neisseria meningitidis* Group B strains.

We obtained capsule-deficient and galE mutants from six of eight of the MAb B5 negative Group B strains (transformations were unsuccessful in the other two strains). These were also negative with MAb B5 using dot blot, whole cell ELISA or immunofluorescence, with the exception of a BZ157 galE cap-mutant that had low level reactivity both by immunofluorescence and dot blot. The MAb B5 strains were characterized using a battery of immunotyping MAbs. We determined the immunotype of the eight MAb B5 negative strains using combinations of the appropriate MAbs (see Methods) and dot blots of WC lysates (obtained from Peter van der Ley) (Table 3). In addition, structural fingerprinting of the inner core region of MAb B5 negative strains was performed by ES-MS on O-deacylated LPS from five of the respective capsule-deficient galE mutants (1000, NGE30, EG327, BZ157, NGH38) (Table 4). Strains 1000, NGE30, EG327 were non-typical by MAbs and LPS from these strains lacked PEtn on HepII of the inner core. BZ157, which corresponded to immunotype L2 by MAbs contained PEtn in the inner core, and by analogy to L2, at the 6/7 position of HepII (Table 3). NGH38 was immunotype L2, L5, and analogous to L2 by structural analysis. Those strains that were non-typable failed to react with MAbs that recognize L3,7,9, L6, L2,5 µL4,6,9. However, 15/17 MAb B5 negative *Neisseria meningitidis* strains (all serogroups) were positive for L2, 5 and all MAb B5 positive strains were positive for L3,7,9. No reaction with any immunotyping MAbs was observed with 8/32 MAb B5 negative strains and 24/68 of MAb B5 positive strains.

Figure 6A:
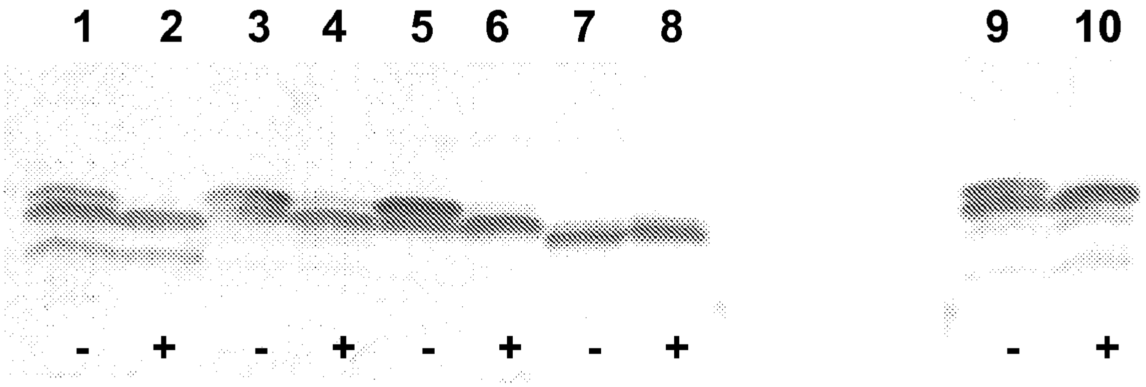
FIGS. 6A and 6B illustrate silver stained tricine gels of LPS preparations from *Neisseria meningitidis* group B strains not reactive with MAb B5. These LPS preparations were either not treated (−) or treated with (+) neuraminidase to show the presence of sialic acid.
Figure 6B:
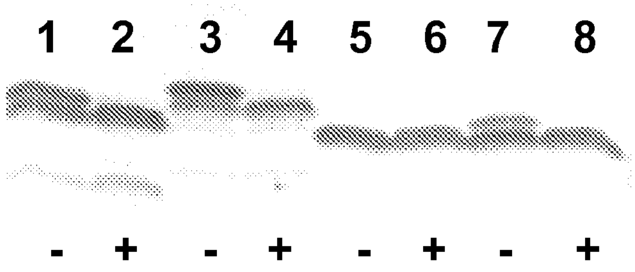

To determine if the degree of sialylation of the LPS was a factor in the ability of MAb B5 to recognize its inner-core epitope, MAb B5 negative strains were examined by LPS gels. MAb B5 reactivity was unaffected by varying the state of sialylation through exposure to neuromimidase as described in methods (FIGS. 6A and 6B). Furthermore, strain MC58, with which the MAb B5 reacted strongly, was found to be highly sialylated (FIG. 6B) and this was confirmed by ES-MS of purified O-deacylated LPS (data not shown). Therefore our data did not support a contribution of sialylation to the lack of MAb B5 reactivity.

With respect to the other *Neisseria* species, MAb B5 also recognized the inner core LPS of five strains of *Neisseria gonorrhoeae* (F62, MS11, FA19, 179008, 150002) (two were negative) and (at least) two strains of *Neisseria lacramica* (L19, L22). However, MAb B5 did not react with one strain each of *Neisseria* polysaccharide (M7), *Neisseria* mucosa (F1), *Neisseria* cinerea (Griffiss, J. M., et al., 1987. Infect. Immun. 55: 1792-1800), *Neisseria* elongata (Q29), *Neisseria* sicca (Q39) and *Neisseria* subflava (U37). Also MAb B5 did not react with *Escherichia coli* (DH5 alpha), *Salmonella typhimurium* (LT2) or its isogenic LPS mutants (rfaC, rfal, rfaP).

Finally, we investigated the reactivity of MAb B5 with 100 strains that included representatives of serogroups A, B, C, W, X, Y and Z (Maiden, M. C. J., et al., 1998. PNAS 95: 3140-3145). Of these strains, 70% were MAb B5 positive. Clustering according to genetic relatedness was evident. For example, none of the MAb B5 negative stains were in the ET5 complex. Among Group A strains, MAb B5 positive and negative stains also fell into distinct clusters. For example, lineages I-III and lineage A4 were positive and lineage IV-I was negative. This collection, together with that described in (Seiler, A., et al., 1996. Mol. Microbiol. 19: 841-856) represents the most complete set available for known hyperinvasive lineages in all major serogroups of *Neisseria meningitidis* strains.

Discussion and Conclusions

The pre-requisites for any candidate *Neisseria meningitidis* Group B vaccine would be that it contains a highly conserved epitope(s) that is found in all Group B stains and is accessible to antibodies in the presence of capsule. Our approach has combined genetics, structural analysis and immunobiology to define candidate epitopes in inner core LPS of *Neisseria meningitidis* Group B. This study uses murine MAb B5, isotype IgG3, which was raised to a genetically defined immunotype L3 galE mutant in order to specifically target inner-core LPS epitopes. The epitope(s) recognized by MAb B5 was defined by cross-reactivity studies with purified LPS glycoforms of known structure. MAb B5 recognized all LPS glycoforms in which the PEtn is at the 3-position of HepII (immunotypes L1, L3, L7, L8, and L9) and failed to react with immunotypes where PEtn is at the 6- or 7-position (L2, L4, and L6) or absent from HepII (L5) (FIGS. 1A-1B). MAb B5 reacted with 70% *Neisseria meningitidis* strains tested from the two most complete sets of *Neisseria meningitidis* strains available word-wide (Seiler, A., et al., 1996. Mol. Microbiol. 19: 841-856, 35). Of these strains, 76% of *Neisseria meningitidis* Group B strains tested were positive with MAb B5 and 70% of a collection that included all *Neisseria meningitidis* serogroups tested were positive with MAb B5. Therefore, it may be envisaged that a vaccine containing a limited number of glycoforms, representing all the possible PEtn positions (none, 3 and 6/7) on HepII on the inner core, would cover 100% of *Neisseria meningitidis* Group B strains.

The LPS structures of MAb B5 negative strains were confirmed by structural analysis. Two structural variants were recognized. One variant without PEtn in the inner core LPS (e.g. NGE30, EG327, 1000); and the other, with PEtn group of HepII (e.g. BZ157, NGH38) at the 6- or 7-position instead of the 3-position.

With a view to developing inner core LPS epitopes as vaccine candidates, it is significant that there were no effects of the capsule on MAb B5 accessibility, as shown by co-localization of the anti-capsule antibody and MAb B5 in wild-type organisms (MC58) grown in vitro and in vivo by confocal microscopy (FIGS. 5A and 5B). Nor did the presence or absence of sialic acid have an effect since both MAb B5 positive and negative strains had high sialylation states as shown by tricine gels (FIGS. 6A and 6B) and confirmed by ES-MS (data not shown).

There was no evidence of phase variation in MAb B5 positive or negative strains in this study, with the exception of one strain (BZ157) which had a very low level of MAb B5 positive strains in parent and galE mutant (0.06%) (data not shown). Structural analysis of LPS extracted from these two variants is currently under investigation.

Three-dimensional space filling models of the inner core LPS of L3 and L4 immunotypes show that the position of the PEtn, either 3- or 6-position respectively, alters the accessibility and conformation of PEtn in the inner core epitope (FIGS. 3A and 3B). The most striking example of the importance of PEtn for MAb B5 reactivity was observed when PEtn was removed from the immunotype L8 (MAb B5 positive) by treatment with hydrogen fluoride (HF) which totally abolished MAb B5 reactivity (FIG. 3C).

Previous studies with oligosaccharide conjugates in mice and rabbits have demonstrated that PEtn is important in immunogenicity and functional activity of polyclonal antibodies (Verheul, A. F., et al., 1991. Med. Immun. 59: 843-851). These studies identified two sets of polyclonal antibodies. One set resulting from L1 and L3,7,9 oligosaccharides had PEtn in the 3-position of HepII, were immunogenic, had opsonophagocytic (OP) and chemiluminescence in oxidative burst reaction, but had no serum bactericidal activity. The other set of antibodies resulting from L2 conjugates (6- or 7-position or without PEtn at HepII) were poorly immunogenic and had greatly reduced OP activity and chemiluminescence (Verheul. A. F., et al., 1991. Infect. Immun. 59: 843-

851). Future studies will look at the safety and immunogenicity of inner core LPS-conjugates (PEtn at 3-position of HepII and alternative glycoforms) and the functional ability of these polyclonal antibodies in opsonic and serum bacterial assays, initially in mice and rabbits. Preliminary studies using MAb B5 in an opsonophagocytosis assays with *Neisseria meningitidis* strain MC58 and donor human polymorphonuclear cells suggest MAb B5 is opsonic in the presence of complement and that the uptake of *Neisseria meningitidis* bacteria correlates with an oxidative burst reaction within the neutrophil. MAbB5 does not appear to have any significant serum bactericidal activity with *Neisseria meningitidis* strain MC58, however this is not unexpected in view of its isotype (IgG3). The functionality of MAb B5 is currently under further investigation.

In conclusion, MAb B5 recognizes a conserved inner core epitope in which the PEtn is at the 3-position of HepII. This epitope was present in 76% *Neisseria meningitidis* Group B strains and 70% of all *Neisseria meningitidis* serogroups, and was accessible in the presence of capsule. A limited number of alternative glycoforms have been identified that are not recognized by MAb B5 where the PEtn is either absent or at an exocyclic position of HepII. Therefore, a vaccine containing a limited number of glycoforms might give 100% coverage of all *Neisseria meningitidis* Group B strains.

TABLE 1

Bacterial strains.

| Species Strain | Relevant immunotype (bold) and genotype (italics) | Source/reference |
|---|---|---|
| *Neisseria meningitidis* | | |
| MC58 | **L3** | CSF isolate Virji, M., et al., 1991. Mol Microbiol 5: 1831-1841 |
| H44/76 | **L3** | Holton, E. 1979. J Clin Microbiol 9: 186-188 |
| MC58 | *galE* | Jennings, M. P., et al., 1993. Mol. Microbiol. 10: 361-369 |
| MC58 | *Isi1(rfaF)* | Jennings, M. P., et al., 1995 Microb. Pathog. 19: 391-407 |
| MC58 | *IgtA* | Jennings, M. P., et al., 1995. Mol. Microbiol. 18: 729-740 |
| MC58 | *IgtB* | Jennings, M. P., et al., 1995. Mol. Microbiol. 18: 729-740 |
| H44/76 | *rfaC* | Stolljokovic, I., et al., 1997. FEMS Microbial. Lett. 15 1: 41-49 |
| H44/76 | *icsA* | van der Ley, P., et al., 1997. FEMS Microbiol. Lett. 146: 247-253 |
| H44/76 | *icsB* | van der Ley, P., et al., 1997. FEMS Microbiol. Lett. 146: 247-253 |
| 126E; 35E; H44/76; 89I; M981 M9926155; 892257; M978; 120M; 7880; 7889; 3200 | **L1-L12 RESPECTIVELY** | Poolman, J. T., et al., 1982. FEMS Microbial. Lett. 13: 339-348 |
| BZ157 | **L2** | Seiler, A., et al., 1996. Mol. Microbiol. 19: 841-856 |
| BZ157 | *galE* | This study |
| 1000 | **NT** | Seiler, A., et al., 1996. Mol. Microbiol. 19: 841-856 |
| 1000 | *galE* | This study |
| NGE30 | **NT** | Seiler, A., et al., 1996. Mol. Microbiol. 19: 841-856 |

TABLE 1-continued

Bacterial strains.

| Species Strain | Relevant immunotype (bold) and genotype (italics) | Source/reference |
|---|---|---|
| NGE30 | *galE* | This study |
| EG327 | **NT** | Seiler, A., et al., 1996. Mol. Microbiol. 19: 841-856 |
| EG327 | *galE* | This study |
| NGH38 | **L2, 5** | Seiler, A., et al., 1996. Mol. Microbiol. 19: 841-856 |
| NGH38 | *galE* | This study |
| EG328 | **NT** | Seiler, A., et al., 1996. Mol. Microbiol. 19: 841-856 |
| EG328 | *galE* | This study |
| 3906; NGH15; BZ133; BZ83; EG329; SWZ107; BZ198; NGH41 NG4/88; 2970; BZ147; NGG40; NGH36; NG3/88; NGF26; NG6/88; NGH38; NGE28; BZ169; 528; DK353; BZ232 DK24; BZ159; BZ10; BZ163; NGP20 | | Seiler, A., et al., 1996. Mol. Microbiol. 19: 841-856 |
| B40; Z4024; Z4081; Z2491; Z3524; Z3906; Z5826; BZ10; BZ163; B6116/77; L93/4286; NG3/88; NG6/88; NGF26; NGE31; DK24; 3906; EG328; EG327; 1000; B534; A22; 71/94; 860060; NGG40; NGE28; NGH41; 890326; 860800; NG4/88; E32; 44/76; 204/92; BZ8; SWZ107; NGH38; DK353; BZ232; E26; 400; BZ198; 91/40; NGH15; NGE30; 50/94 88/03415; NGH36; BZ147; 297-0 | | (35) |
| *Neisseria lactamica* (L12.L13.L17, L18, L19, L20, L22) *polysaccharea* (P4) *mucosa* (M7), *cinerea* (F1), *elongata* (I8), *sicca* (Q29), *subflava* (U37) | | Brian Spratt & Noel Smith |
| *Neisseria gonorrhoeae*: | | |
| F62, MS11, FA19, FA1090, 179008, 150002, 15253 | | R. Goldstein |
| SN-4 | | Staffan Normavk |
| P9-2 | | M. Virji |
| *Haemophilus influenzae* type b | | Hood, D. W., et al., 1996. Mol. Microbiol. 22: 951-964 |
| Eagan; 7004; Rd5B33; 3Fe; E3Fi; E1B1 | *opsx rfaF orfH. IpxA* | |
| PLAK33 | | Steeghs, L., et al., 1998. Nature 392: 449-450. |
| *Haemophilus somnus* 738 L1 | | J. Richards |
| Non-typable | | J. Eskola |

TABLE 1-continued

| Bacterial strains. | | |
|---|---|---|
| Species Strain | Relevant immunotype (bold) and genotype (italics) | Source/reference |
| *Haemophilus influenzae* | | |
| (NTHI): 54, 375, 477, 1003, 1008, 1042, 1147, 1231 | | |
| *E. coil* DH5α | | Neidardt, F. C., et al., (ed.), ASM Press. |
| *Salmonella typhimurium* LT2 | *rfaC; rfa1; rfaP* | Schnaitman, C. A., and F. D. Klena. 1993. 57: 655-682 |

TABLE 4

Negative ion ES-MS data and proposed compositions of 0-deacylated LPS from galE capsule-deficient mutant *Neisseria meningitidis* MAb B5 negative strains. Average mass units were used for calculation of molecular weight based on proposed composition as follows: Glc, 162.15; Hep, 192.17; GlcNAc, 203.19; Kdo, 220.18; PEtn, 123.05.

| | Observed Ions (m/z) | | Molecular Mass (Da) | | |
|---|---|---|---|---|---|
| Strain | $(M-2H)^{2-}$ | $(M-H)^{-}$ | Observed | Calculated | Lipid A[b] |
| 1000 | 1213.0 | 2427.6 | 2427.7 | 24270.2 | 1075 |
| | 1252.9 | 2507.8 | 2507.8 | 2507.2 | 1155 |
| | 1314.5 | 2630.9 | 2603.9 | 2630.3 | 1278 |
| NGH38 | 1293.8 | 2589.5 | 2589.3 | 2589.3 | 952 |
| EG327 | 1151.2 | 2304.4 | 2304.4 | 2304.1 | 952 |
| NGE30 | 1132.1 | — | — | 2265.1 | 1075 |
| | 1396.1 | 2793.4 | 2793.7 | 2792.5 | 1075 |

TABLE 2

Reactivity of monoclonal antibody B5 with representative *Neisseria meningitidis* strains of immunotypes L1-L12 determined by whole cell ELISA, dot blots of lysates, immunofluorescence and confocal microscopy.

| Strain | Serogroup: Serotype: | Immuno-type | Whole cell ELISA[a]($OD_{A405\ nm}$) | Dot Blot[b] | Immuno-fluorescence[c] |
|---|---|---|---|---|---|
| 126E | C: 3: P1.5, 2 | L1 | +1.8 | +++ | + |
| 35E | C: 20:P1.1 | L2 | −<0.4 | − | − |
| H44/76 | B.15.P1.7, 1 | L3 | +1.3 | +++ | ++ |
| 89I | C: nt: P1.16 | L4 | −<0.4 | − | − |
| M98I | B: 4: P1.— | L5 | −<0.4 | +/− | − |
| M992 | B: 5: P1.7, 1 | L6 | −<0.4 | +/− | − |
| 6155 | B: nt: P1.7, 1 | L7 | +0.8 | ++ | + |
| M978 | B: 8: P1.7, 1 | L8 | +1.9 | +++ | ++ |
| 892257 | B: 4: P1, 4 | L8 | +1.9 | | |
| 120M | A: 4: P1.10 | L9 | +1.8 | +++ | + |
| 7880 | A: 4: P1: 6 | L10 | +2.2 | +++ | + |
| 7889 | A: 4: P1.9 | L11 | +2.0 | +++ | ++ |
| 3200 | A: 4: P1.9 | L12 | +2.1 | +++ | ++ |

[a]Positive reactivity ($OD_{A405}$ > 0.4) (+), negative reactivity ($OD_{A405}$ < 0.4) (−)
[b]Strongly positive (+++), positive (++), weakly positive (+/−), negative (−).
[c]Strongly positive (++), positive (+), negative (−).

TABLE 3

Correlation between reactivity with monoclonal antibody B5, immunotyping and location of phosphoethanolamine (PEtn) on HepII of inner core.

| | | | Position of PEtn on HepII | |
|---|---|---|---|---|
| Strain | Mab B5 | Immuno-type* | O-3 | O-6 |
| MC58 | + | L3, 7 | + | − |
| 1000 | − | NT | − | − |
| NGE30 | − | NT | − | − |
| EG37 | − | NT | − | − |
| BZ157[#] | − | L2, 5 | − | + |
| BZ157[§] | + | L3, 7 | + | − |
| NGH38 | − | L2, 5 | − | + |

Abbreviations: NT = non-typable
*MN4A8B2 (L3, 7, 9); MN42F12.32 (L2, 5); MN4C1B (L4, 6, 9); MN40G11.7 (L6)
[#]BZ157 MAb B5 negative variant
[§]BZ157 MAb B5 positive variant TABLE 4-continued Negative ion ES-MS data and proposed compositions of 0-deacylated LPS from galE capsule-deficient mutant *Neisseria meningitidis* MAb B5 negative strains. Average mass units were used for calculation of molecular weight based on proposed composition as follows: Glc, 162.15; Hep, 192.17; GlcNAc, 203.19; Kdo, 220.18; PEtn, 123.05.

| Strain | $(M-2H)^{2-}$ | $(M-H)^{-}$ | Observed | Calculated | Lipid A[b] |
|---|---|---|---|---|---|
| | 1436.0 | 2873.7 | 2873.9 | 2872.5 | 1155 |
| | 1498.0 | 2997.2 | 2997.1 | 2995.6 | 1278 |
| BZ157 | 1274.6 | 2551.4 | — | 2550.3 | 1075 |
| | 1314.8 | 2631.1 | 2631.2 | 2630.3 | 1155 |
| | 1376.4 | 2754.4 | 2754.5 | 2753.4 | 1278 |
| | 1457.5 | 2916.6 | 2916.6 | 2915.6 | 1278 |

| Strain | Proposed Composition[a] |
|---|---|
| 1000 | 2Glc, GlcNAc, 2Hep, 2 Kdo, Lipid A |
| | 2Glc, GlcNAc, 2Hep, 2 Kdo, Lipid A |
| | 2Glc, GlcNAc, 2Hep, 2 Kdo, Lipid A |
| NGH38 | 3Glc, GlcNAc, 2Hep, PEtn, 2Kd0, Lipid A |
| EG37 | 2Glc, GlcNAc, 2Hep, 2 Kdo, Lipid A |

TABLE 4-continued

Negative ion ES-MS data and proposed compositions of 0-deacylated LPS from galE capsule-deficient mutant *Neisseria meningitidis* MAb B5 negative strains. Average mass units were used for calculation of molecular weight based on proposed composition as follows: Glc, 162.15; Hep, 192.17; GlcNAc, 203.19; Kdo, 220.18; PEtn, 123.05.

| | |
|---|---|
| NGE30 | Glc, GlcNAc, 2Hep. 2Kdo, Lipid A |
| | 3Glc, 2GlcNAc, 2Hep, 2 Kdo, Lipid A |
| | 3Glc, 2GlcNAc, 2Hep, 2 Kdo, Lipid A |
| | 3Glc, 2GlcNAc, 2Hep, 2 Kdo, Lipid A |
| BZ157 | 2Glc, GlcNAc, 2Hep, PEtn, 2Kd0, Lipid A |
| | 2Glc, GlcNAc, 2Hep, PEtn, 2Kd0, Lipid A |
| | 2Glc, GlcNAc, 2Hep, PEtn, 2Kdo, Lipid A |
| | 3Glc, GlcNAc, 2Hep, PEtn, 2Kd0, Lipid A |

[a]Glc, glucose; GlcNAc, N-acetylglucosamine; PEtn, phosphoethanolamine; Hep, heptose; Kdo, 3-deoxy-D-manno-octulosonic acid.
[b]As determined by MS-MS analyses.

Example 2

Identification of Additional Inner Core Epitopes

Introduction

Example 1 identifies an inner core LPS epitope that was accessible and conserved in 70% of a global collection of 104 *Neisseria meningitidis* strains representative of all major serogroups (Plested et al., 1999, Infect. Immunity 67: 5417-5426). The epitope recognized by MAb B5 was identified in all LPS immunotypes with phosphoethanolamine (PEtn) in the 3-position of β-chain heptose (HepII) of inner core LPS. Further work was carried out to identify additional epitopes, with the aims outlined in FIG. 4.

In summary

A series of twelve murine monoclonal antibodies (MAbs) were developed at NRC, by using a procedure described previously by us (Plested et al., 1999 Infect. Immunity 67: 5417-5426) except using formalin-fixed *Neisseria meningitidis* L4 (strain 891) galE whole-cells. The twelve MAbs were extensively screened by ELISA using purified LPS from *Neisseria meningitidis* mutants and wild-type strains and three MAbs B2 (IgG2b), A4 (IgG2a), and A2 IgG2a were chosen for further investigation. Conservation of the inner core LPS epitope was assessed at Oxford using wild-type whole-cell lysates of a global collection of 104 *Neisseria meningitidis* disease isolates (Maiden, M. C. J., et al., 1998. PNAS 95: 3140-3145). Accessibility of the inner core LPS epitope was assessed using immunofluorescence microscopy with ethanol-fixed *Neisseria meningitidis* whole-cells of wild type and mutants adherent to a monolayer epithelial cells (Plested et al., 1999).

Each of the three MAbs reacted with purified *Neisseria meningitidis* L4 galE LPS by ELISA. Except for MAb B2 that had low reactivity with *Neisseria meningitidis* L4 LPS, none of the *Neisseria meningitidis* L4 series of MAbs were able to the recognize wild-type L4 or L2 purified LPS by ELISA. None of the *Neisseria meningitidis* L4 MAbs recognized *Neisseria meningitidis* wild-type L2 or L4 whole-cells by immunofluorescence microscopy.

MAb B2 reacted with 15/32 *Neisseria meningitidis* MAb B5 negative *Neisseria meningitidis* strains and 9/68 *Neisseria meningitidis* MAb B5 positive *Neisseria meningitidis* strains by whole-cell dot blot analysis. MAb 2 reacted with L4 galE, L4 wild-type (very low reactivity) but not L3 galE, L2 galE (native) O-deacylated (odA)), L2 wild-type (native-odA), L5, L6 wild-type LPS.

MAb A2 recognized 28/32 *Neisseria meningitidis* MAb B5 negative *Neisseria meningitidis* strains and 20/68 *Neisseria meningitidis* MAb B5 positive *Neisseria meningitidis strains by whole-cell dot blot analysis. MAb A*2 reacted with L4 galE (native/odA), L2 galE (native) but not L3 galE, L2 galE (odA), L2 wild-type (native/odA), L4, L5, L6 wild type LPS.

MAb A4 reacted with 29/32 *Neisseria meningitidis* MAb B5 negative *Neisseria meningitidis* strains and 24/68 *Neisseria meningitidis* MAb B5 positive *Neisseria meningitidis* strains by whole-cell lysate dot blot analysis. MAb A4 reacted with L4 galE, L2 galE (native/odA), but not L3 galE, L2 wild type, L4, L5, L6, L8 wild-type LPS.

Based on these results, MAb A4 (IgG2a) was chosen for further study as it demonstrated specificity for both L4 galE and L2 galE LPS by ELISA and recognized all except 3 *Neisseria meningitidis* B5 negative *Neisseria meningitidis* strains (BZ232 serogroup B; NGH38 serogroup B; F1576 serogroup C). Together MAbs B5 and A4 were able to recognize 97/100 *Neisseria meningitidis* isolates. Immunofluorescence microscopy demonstrated that MAb A4 was able to access the inner core epitope in an L4 galE mutant in the presence of capsule.

We have identified LPS inner-core epitopes with PEtn at the 3-position of HepII (MAb B5) or not at the 3 position (MAb A4). There remain 3 strains out of 100 (BZ232, NGH38 and F1576) which show no reactivity with either MAb A4 or MAb B5. The structural basis for this non-reactivity is under investigation. Once all the variant glycoforms of the inner core are known, of which at least 3 have been identified, the rationale will exist for including epitopes, representative of all *Neisseria meningitidis* strains causing invasive disease, in a conjugate vaccine. This will be tested for proof in principle using studies in animals before proceeding to human trials.

The following techniques were used:

(1) Murine MAb A4 (IgG2a) was raised to galE (891, L4 immunotype) and selected on basis of reactivity in LPS ELISA & immunofluorescence (IF) microscopy.

(2) LPS ELISA (Plested et al., 2000. J. Immunol. Meth. 237: 73-84): Microtitre plates (Nunc) coated with purified (galE) LPS (10 μg/ml) overnight, were washed, blocked, incubated with MAb for 1 h, washed and detected with anti-mouse IgG alkaline phosphatase and p-NPP ($OD_{A405\ nm}$).

(3) Immunoblotting using whole-cell lysates from 104 *Neisseria meningitidis* strains (Plested et al., 1999 IAI 67: 5417-5426). MAb A4 was detected using anti-mouse IgG alkaline phosphatase and BCIP/NBT.

(4) Immunofluorescence microscopy: as before (Plested et al., 1999 IAI 67: 5417-5426) or *Neisseria meningitidis* were adherent to cultured human buccal epithelial cell line (16HBE140) instead of HUVECs; fixed, blocked, incubated with MAb A4 and anti-capsular serogroup B antibody then detected using fluorescently labeled secondary antibodies (TRITC or FITC).

(5) Fine structural analysis of purified O-deacylated LPS samples by negative-ion ES-MS and NMR (Plested et al., 1999 IAI 67: 5417-5426).

Results:

1) Accessibility of LPS epitope in *Neisseria meningitidis* whole-cells.

See FIGS. 7A-7E.

Figure 7A:
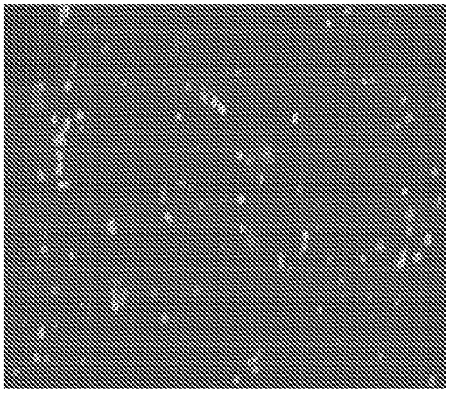
Figure 7B:
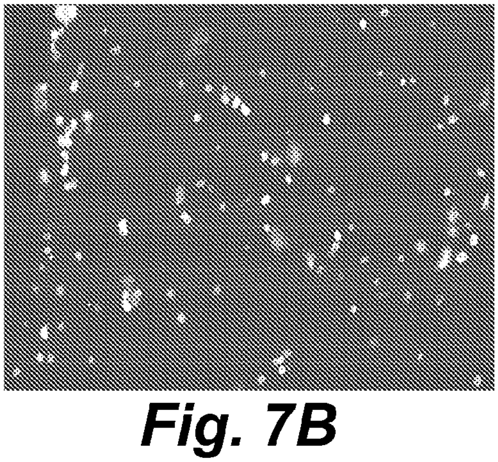
Figure 7C:
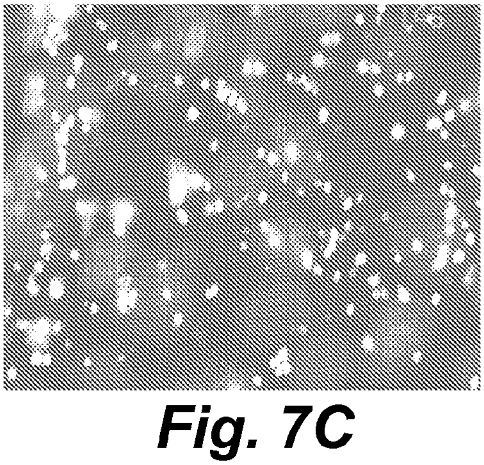

MAb A4 accesses the inner core LPS epitope in *Neisseria meningitidis* L4 galE mutant in the presence of capsule (magnification ×100). *Neisseria meningitidis* L4 galE adherent to epithelial cells (16HBE140) stained with:

FIG. 7A: MAb A4 (anti-mouse TRITC-red);

FIG. 7B: anti-cap B (anti-rabbit FITC-green);

FIG. 7C: triple staining with MAb A4 (anti-mouse TRITC-red), anti-cap B (anti-rabbit FITC-green) and epithelial cells stained DAPI (blue).

Figure 7D:
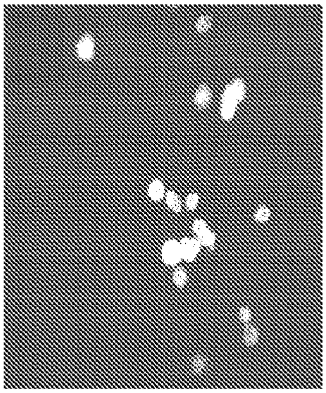
FIGS. 7D and 7E illustrate MAb B5 accesses inner core LPS epitopes in *Neisseria meningitidis* L3 MC58 (magnification ×2400).
Figure 7E:
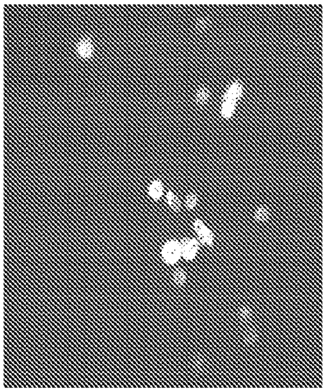

MAb B5 accesses inner core LPS epitopes in *Neisseria meningitidis* L3 MC58 (magnification ×2400). *Neisseria meningitidis* L3 MC58 adherent to HUVECs stained with:

FIG. 7D: MAb B5 (antimouse TRITC-red);

FIG. 7E: anti-cap B (anti-rabbit FITC-green) using confocal immunofluorescence microscopy.

2) Conservation of LPS Epitope Across all Serogroup of *Neisseria meningitidis*

Figure 8:
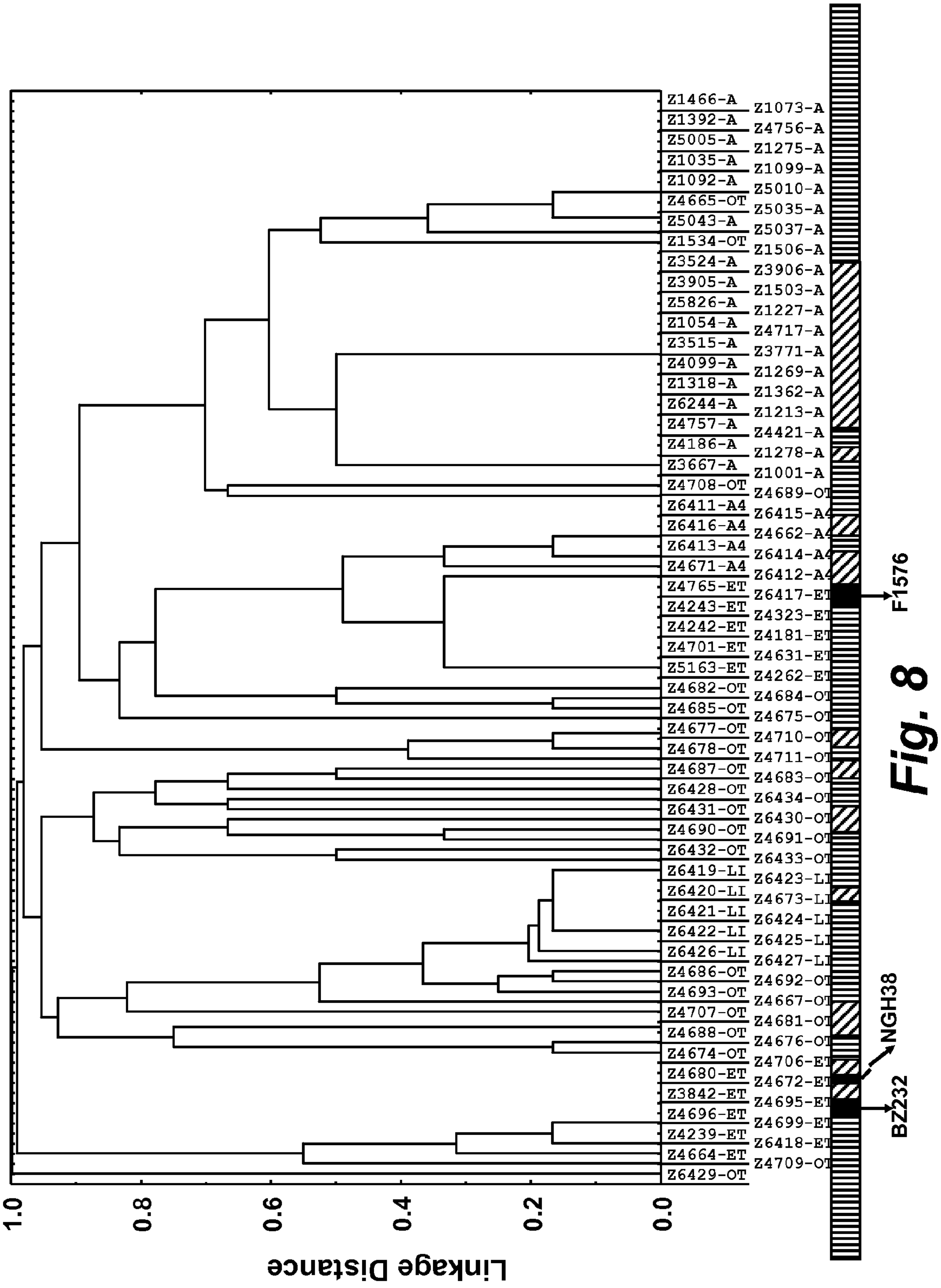
FIG. 8 illustrates conservation of the LPS epitope across *Neisseria meningitidis* serogroups.

See FIG. 8

MAb A4 (diagonal hatched) and MAb B5 (horizontal lines) together recognize all *Neisseria meningitidis* strains by immunoblotting with whole-cell lysates, except 3 strains (black arrows) which are under further analysis. The dendrogram of genetic relationship of *Neisseria meningitidis* strains from a global collection was constructed by cluster analysis following Multi-Locus Sequence Typing (MLST) (Maiden et al., 1998. PNAS 95: 3140-3145).

3) Genetically Defined LPS Structure

See FIGS. 3A-3C.

Fine LPS structural details demonstrate conformational effects of PEtn on epitope presented. Space-filling 3-D molecular models of (Monopolies Monte Carlo) calculated lowest energy states of core LPS from galE mutants [[a]] FIG. 3A: L3; [[b]] FIG. 3B: L4; [[c]] FIG. 3C: L8 (dephosphorylated). Kdo in grey, Heptose (Hep) in red, Glucose (Glc) and Glucosamine (GlcNAc) in light and darker green, (PEtn) in brown.

Conclusions

Inner core glycoforms have been identified with PEtn in the 3-position of HepII, an exocyclic position of Hep II or absent. This study has indicated that utilization of MAb A4 in conjunction with MAb B5 enables 97% of meningococcal strains to be recognized. These studies therefore indicate that inner core LPS may have potential as a *Neisseria meningitidis* serogroup B vaccine.

Example 3

Studies on the Functional Activity of Monoclonal Antibody, MAb 85, and Inner Core (galE) Lipopolysaccharide Antibodies in Human Serum Using an Opsonophagocytosis Assay, a Serum Bactericidal Assay and an In Vivo Passive Protection Model Introduction We have generated a monoclonal antibody, MAb B5. This antibody is accessible to inner core LPS structures in *Neisseria meningitidis* in the presence of capsule and is conserved in 70% of a representative collection of *Neisseria meningitidis* of all strains and 76% of serogroup B strains (Plested, J. S. et al., 1999. Infect. Immun. 67 (10): 5417-5426).

Until now it was not known if antibodies in a natural human infection can be specific for MAb B5 epitope and have functional activity.

MAb B5 has been shown to have opsonic and bactericidal activity against galE mutant and ability to passively protect infant rats against challenge with *Neisseria meningitidis* galE mutant using an in vivo model.

Methods (1) Opsonophagocytosis (OP) assay (Plested et al., 2000b): Briefly, fluorescently labeled ethanol-fixed *Neisseria meningitidis* MC58 or galE mutant or beads coated with purified galE LPS (10 g/ml) were opsonised with MAb B5 and human complement source diluted in final buffer for 10 mins/37° C./500 rpm in microtitre plate. Then human peripheral blood polymorphonuclear cells (PMNs) prepared from heparinized donor blood were diluted in final buffer and added to each well ($1\times10^7$ cells/ml) and incubated for a further 10 min/37° C./500 rpm. Reaction mixture was stopped on ice by addition of 150 μl PBS-EDTA and added to FACS tube containing 50 μl TRYPAN BLUE. Mixture was mixed and 10,000 lymphocytes were analyzed on FACSCAN and CELLQUEST software. PMNs were analyzed by FSC vs appropriate channels to determine % uptake of fluorescent bacteria by granulocytes and monocytes (% OP activity).

(2) Serum Bactericidal (SB) assay method was adapted from CDC protocol except MAb B5 was added to dilutions of human pooled sera and 1000 cfu of *Neisseria meningitidis* strain and incubation time was 40-45 min at 37° C. Briefly, bacteria were grown up onto BHI agar overnight from frozen stocks. A suspension of bacteria in PBS-B was measured at $OD_{260}$(1:50 in 1% SDS, 0.1% NaOH). Using a 96-well microtitre plate 50 μl buffer was added to wells in columns 2-7. 50 μl of 80% decomplemented human pooled sera was added to column 8 wells. 100 μl of 80% pooled sera was added to wells in column 1. Two-fold serial dilutions of antibody were added to columns 1-7 (discarding the last 50 μl from column 7). 50 μl of bacterial suspension diluted to give 1000 cfu in 50 μl were added to wells of columns 1-8. The mixture was incubated for 40-45 minutes and plated out onto BHI agar for overnight incubation. The number of colonies on each plate was counted and the results expressed as a % of cfu/ml in decomplemented control well.

(3) In vivo passive protection model using 5-day old Wistar infant rat model. This model was as described by Moe, G. R., et al., 1999. Infect. Immun. 67: 5664-5675, except higher doses of *Neisseria meningitidis* bacteria were used and different *Neisseria meningitidis* strain was used. Briefly, groups of 5 day old infant rats were randomized with mothers. Weighed and given inoculum $1\times10^8$ cfu/ml *Neisseria meningitidis* galE mutant mixed 1:1 with either (i) No antibody (PBS) (ii) Affinity purified MAb B5 (10 μl) (iii) Affinity purified MAb B5(100 pg) (iv) MAb 735 (anticapsular group B antibody) (2 μg). Infant rats were monitored for signs of infection and sampled by tail vein bleed at 6 hours post-infection. Animals were weighed and terminal bleed was taken after 24 h by cardiac puncture following injection of pentobarbitone. Neat and diluted blood were plated immediately onto BHI plates and incubated overnight. Plates were counted next day to determine bacteremia (cfu/ml) at 6 h and 24 h.

(4) LPS ELISA (Plested er al., 2000a. Microtitre plates (NUNC) coated with purified (galE) LPS (10 μg/ml) overnight, were washed, blocked and incubated with MAb or human sera for 1 h, washed and detected with anti-mouse or anti-human IgG alkaline phosphatase and p-NPP ($OD_{A405nm}$).

(5) Affinity purified MAb 85. Spent culture supernatant from MAb B5 was purified on Protein A-SEPHAROSE column and eluted with Glycine pH 4.0, neutralized with Tris-HC1 pH9.0. Fractions were tested for reactivity on LPS ELISA, pooled and concentrated using Amicon-filter. Purity was determined by SDS-PAGE gel and protein concentration was determined by OD and protein assay.

6) FACS surface labeling of *Neisseria meningitidis* bacteria. The method was adapted from Moe, G. R., et al., 1999. Infect. Immun. 67: 5664-5675) except no sodium azide was included in the blocking buffer step (Plested et al., 2000b). To prepare labeled bacteria *Neisseria meningitidis* (strain MC58, galE) organisms were grown overnight by standard conditions at 37° C. on BHI agar plates and gently suspended in PBS. $OD_{A260\ nm}$ was adjusted to give the required concentration e.g. $5\times10^9$ org./ml. 100 µl bacterial cells were added to each FACS tube ($5\times10^8$ org.) and an equal volume of diluted sera (1/100 MAb B5 in 1% BSA/PBS) was added. Tubes were incubated for 2 hours at 4° C. and cells centrifuged for 5 minutes at 13,000 g. The supernatant was discarded and cells were washed with 200 µl of 1% BSA/PBS. 100 µl of FITC-conjugated $F(ab)_2$ goat anti-mouse(Sigma F2772) was added, diluted 1:100 in 1% BSMBS, and tubes were incubated for 1 hour at 4OC. Cells were centrifuged at 13,000 g for 5 minutes and washed by addition of 200 µl of 1% BSMBS. The supernatant was discarded and the cells were suspended in 1% v/v formaldehyde. Samples were transferred to FACSCAN tubes and analyzed on the FACS.

Results

1) Clinical Relevance of MAb B5 Epitope

Figure 10A:
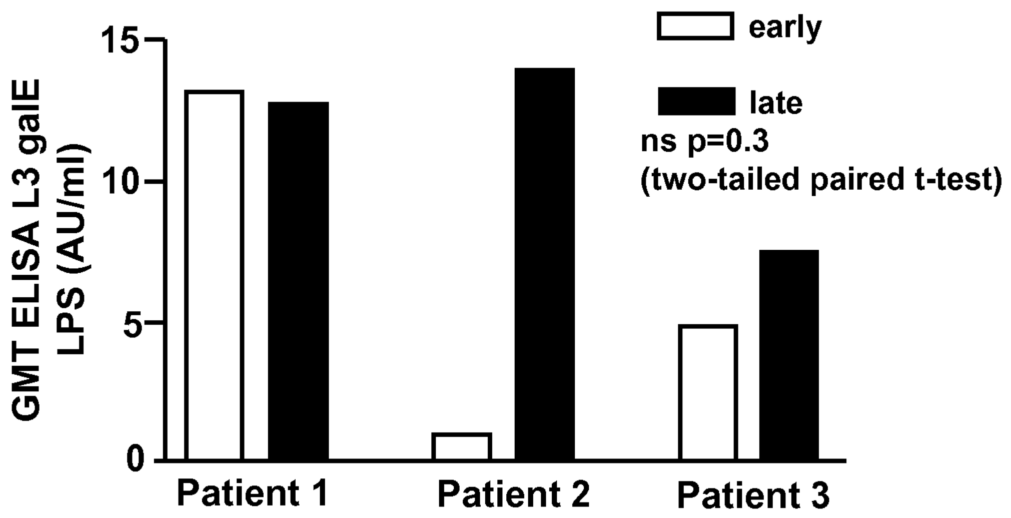
FIG. 10A illustrates ELISA titres of antibodies to L3 galE LPS (IgG) in paired sera taken early and late from children with invasive meningococcal disease.
Figure 10B:
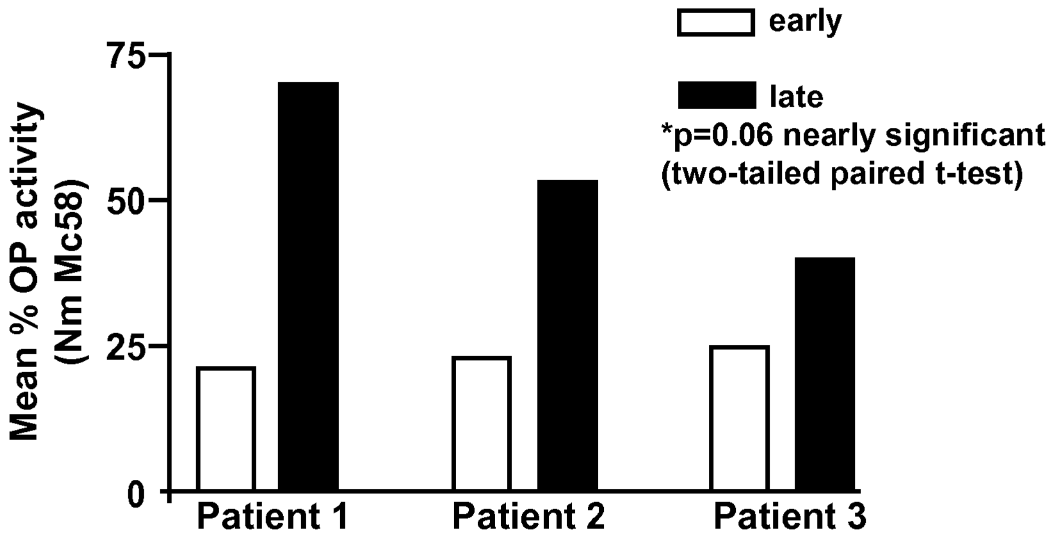
FIG. 10B illustrates mean % phagocytosis of *Neisseria meningitidis* MC58 with paired sera taken early and late from children with invasive meningococcal disease with human peripheral blood mononuclear cells and human complement.

We present data on three paired sera taken from infants early (acute) and later (convalescent) during culture confirmed invasive meningococcal disease (IMD) that resulted from infection with *Neisseria meningitidis* isolates of immunotypes L1, L3 (MAb B5 reactive) (patients 1 and 2) and L2 immunotype (MAb B5 non-reactive) (patient 3) (FIGS. 10A and 10B). The *Neisseria meningitidis* isolates for patients 1, 2, 3 were L1 (B nt p1.14), L3 (B15 p1.7) and L2 (C2a p1.5) respectively. One paired sera from patient 2 infected with a *Neisseria meningitidis* strain that was MAb B5 reactive demonstrated an increase in specific inner core LPS antibodies by ELISA between early and late infection (p=0.03 not significant two-tailed paired t-test, 95% Cl 0.09-90.8)) (FIG. 10A). Patient 1 sera demonstrated no significant difference in the titre of antibody taken early and later during IMD but the titer of the early sample was already at a high level (FIG. 10A). The lack of increase may reflect higher affinity antibody in the convalescent sample that would not be detected in this ELISA. However in both patient 1 and 2 sera there was a nearly significant increase in functional activity in the convalescent sera in an opsonophagocytosis assay with L3 wild-type strain MC58 and human peripheral polymorphonuclear cells (p=0.06 two-tailed paired t-test, 95% Cl 0.90-5.96) (FIG. 10B) (Plested et al., 2000b). There was no significant increase in specific antibody titre between acute and convalescent sera taken from patient 3 infected with L2 immunotype strain (MAb B5 non-reactive) as measured by ELISA (FIG. 10A). There was no significant functional activity in OP assay against L3 wild-type strain with sera taken from patient 3 early or later during IMD (FIG. 10B). This demonstrates the clinical relevance of the MAb B5 epitope in vivo and that specific inner core LPS antibodies are functional in vivo.

2) Supporting Evidence that Murine MAb B5 has Functional Activity in Biologically Relevant Assays and an In Vivo Model.

(i) Opsonophagocytosis Assay

The OP assay provides evidence that MAb B5 has opsonic activity against *Neisseria meningitidis* wild type and galE mutant and that the OP activity is specific far MAb B5 epitope.

Figure 11A:
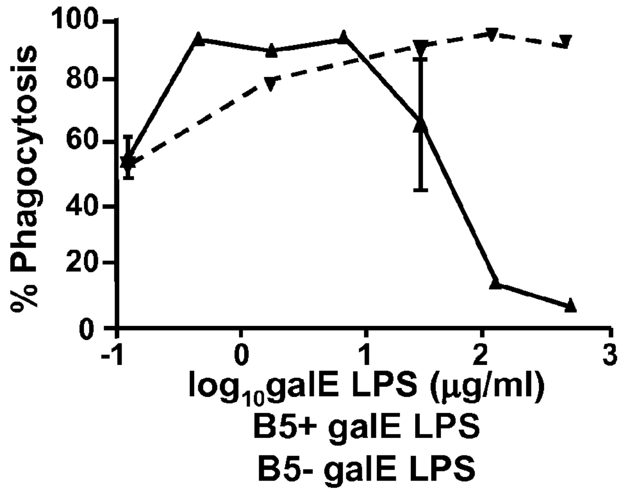
FIG. 11A illustrates mean % phagocytosis of *Neisseria meningitidis* MC58 with MAb B5 pre-incubated with increasing concentrations of either (i) B5 reactive or (ii) B5 non-reactive galE LPS with human peripheral blood polymorphonuclear cells and human complement.

The specificity of MAb B5 reactivity using wild-type *Neisseria meningitidis* MC58 was shown by inhibition studies. MAb B5 was pre-incubated with different concentrations of purified LPS. There was a dose response inhibition in OP activity with *Neisseria meningitidis* MC58 with increasing concentrations of galE LPS added to MAb B5 (see FIG. 11A).

Figure 11B:
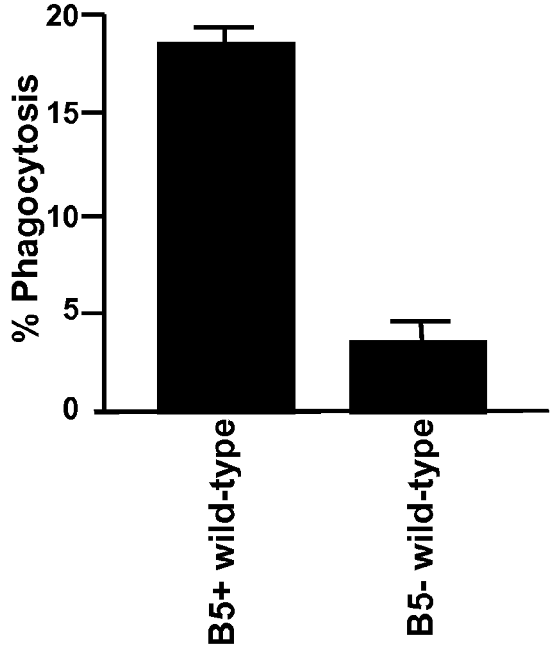
FIG. 11B illustrates mean % phagocytosis of pair of *Neisseria meningitidis* wild-type isogenic strains (*Neisseria meningitidis* BZ157) that are either MAb B5 reactive or B5 non-reactive with MAb B5 as the opsonin with human peripheral blood mononuclear cells and human complement.

MAb B5 has specific OP activity for MAb B5 reactive strains using an isogenic pair of *Neisseria meningitidis* wild-type strains (*Neisseria meningitidis* BZ157, serogroup B) that are MAb B5 reactive or MAb B5 non-reactive. MAb B5 has opsonic activity with MAb B5reactive strain but not MAb B5 non-reactive strain (see FIG. 11B).

Figure 11C:
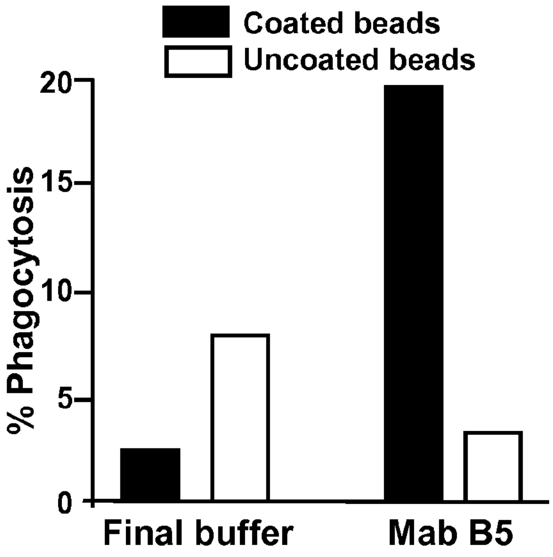
FIG. 11C illustrates mean % phagocytosis of fluorescent latex beads coated with either purified LPS from L3 galE mutant (10 μg/ml) or uncoated, in the presence of MAb B5 or final buffer, with human peripheral blood mononuclear cells and human complement.

OP assay demonstrated the uptake of beads coated with purified L3 galE LPS opsonised with MAb B5 was significantly greater than the uptake with uncoated beads. This demonstrates the specificity of MAb B5 for galE LPS coated onto beads (see FIG. 11C).

(ii) Serum Bactericidal Assay

The SB assay provides evidence that MAb B5 has bactericidal activity against *Neisseria meningitidis* galE mutant in SB assay in the presence of a human complement source (see method).

Figure 12:
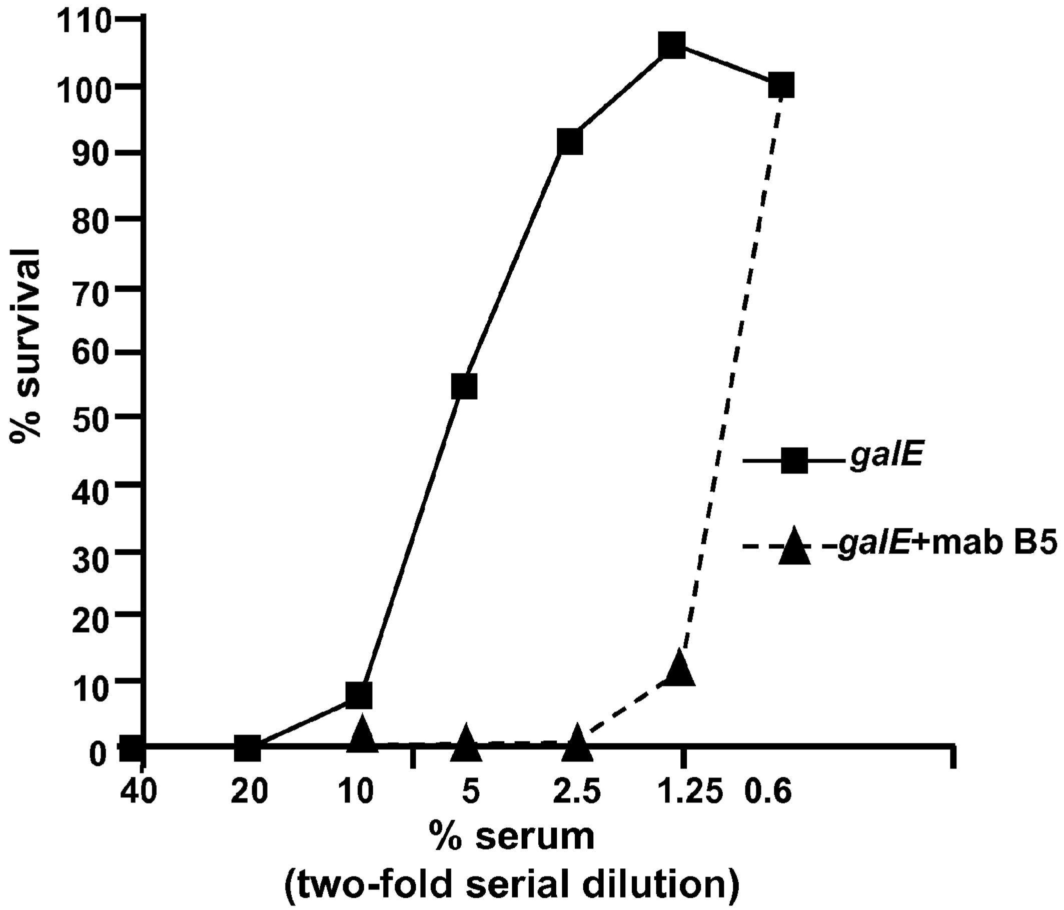
FIG. 12 illustrates mean % survival of *Neisseria meningitidis* galE mutant in the presence and absence of MAb B5 against two-fold serial dilutions of human pooled serum starting at 40% as detected using a serum bactericidal assay (see methods).

The serum sensitivity of galE mutant with either no antibody or in the presence of MAb B5 was compared (FIG. 12). There was a dose response increase in bactericidal activity of galE mutant shown by decreasing ° A) survival, with decreasing % of serum in the presence of MAb B5 compared to no antibody.

(iii) Passive Protection Model Using the Infant Rat

Figure 13:
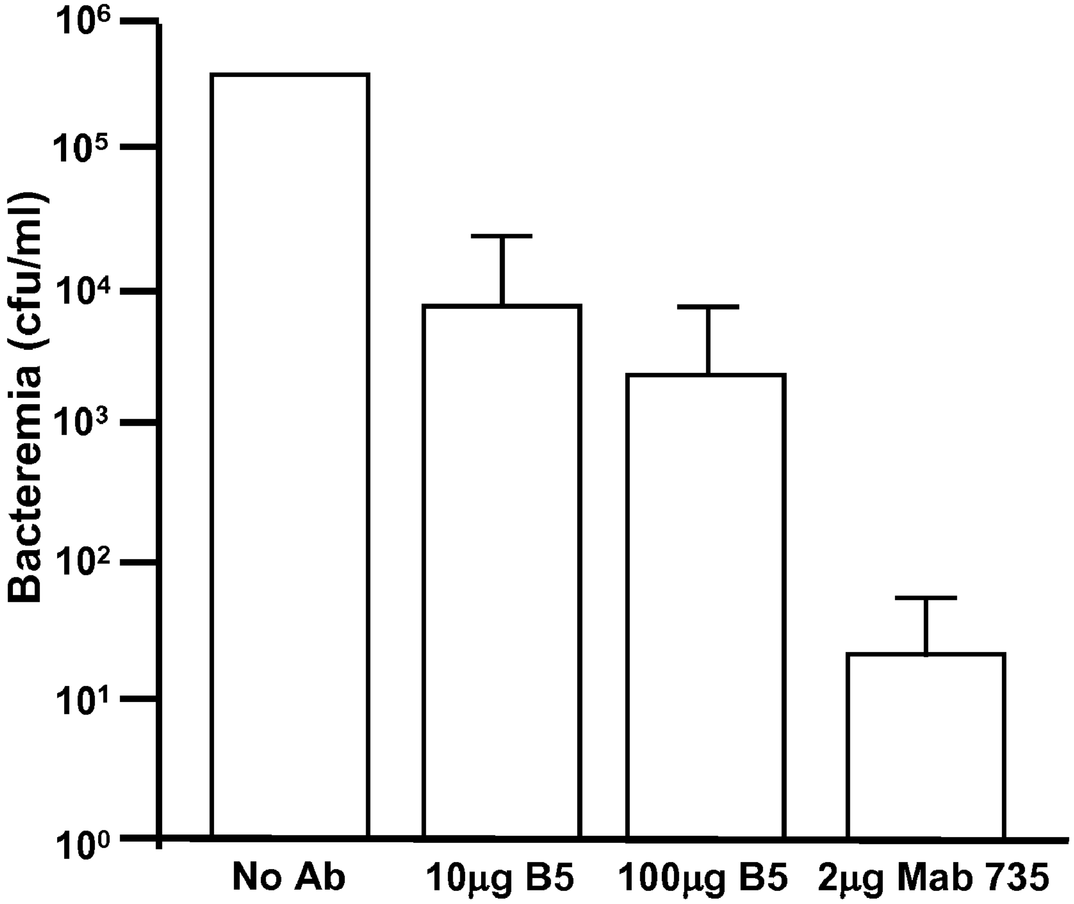
FIG. 13 illustrates geometric mean bacteremia in the blood of groups of 5 day old infant rats 24 h post-infection with $1\times10^8$ cfu/ml galE mutant given simultaneously with: (i) no antibody; (ii) MAb B5 (10 μg dose); (iii) MAb B5 (100 μg dose); or (iv) MAb 735, a positive control anti-capsular antibody (2 μg dose).

Using the 5-day-old infant rat model we have demonstrated that two doses MAb B5 are able to reduce bacteremia against challenge with $1\times10^8$ cfu/ml *Neisseria meningitidis* MC58 galE mutant i.p. compared to no antibody controls. This data demonstrates the ability of MAb B5 to passively protect against challenge with *Neisseria meningitidis* MC58 galE mutant and correlates with the functional activity of MAb B5 in OP and SB assays against the same *Neisseria meningitidis* strain, as shown in FIG. 13.

MAb 85 Binding Studies

Additional evidence that MAb B5 recognizes both wild-type and galE mutant LPS is shown in the following binding studies:

a) Western Blot Analysis

Figure 14:
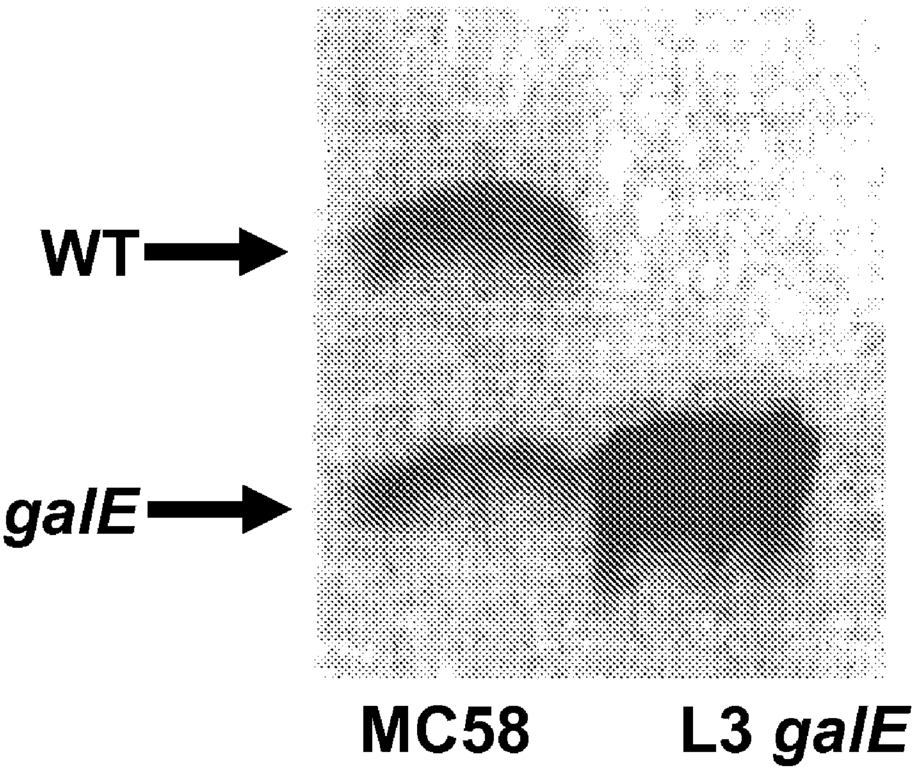
FIG. 14 illustrates a Western blot showing purified LPS from *Neisseria meningitidis* MC58 and galE mutant probed with MAb B5 (ascites fluid 1:2000) detected using anti-mouse IgG alkaline phosphatase and BCIP/NBT substrate.

Purified LPS from wild type *Neisseria meningitidis* MC58 and galE mutant was separated on standard Tricine gel and blotted onto nitrocellulose by standard methods. The blot was probed with MAb B5 culture ascites (1:2000) overnight and detected using anti-mouse IgG and BCIP/NBT substrate. The blot demonstrates binding of MAb B5 to higher molecular weight wild-type LPS band and lower molecular weight galE LPS band in wild-type LPS. This demonstrates that MAb B5 can access and b i d to the wild-type LPS as well as truncated galE LPS, as shown in FIG. 14.

b) FACS Surface Labeling Data

Figure 15A:
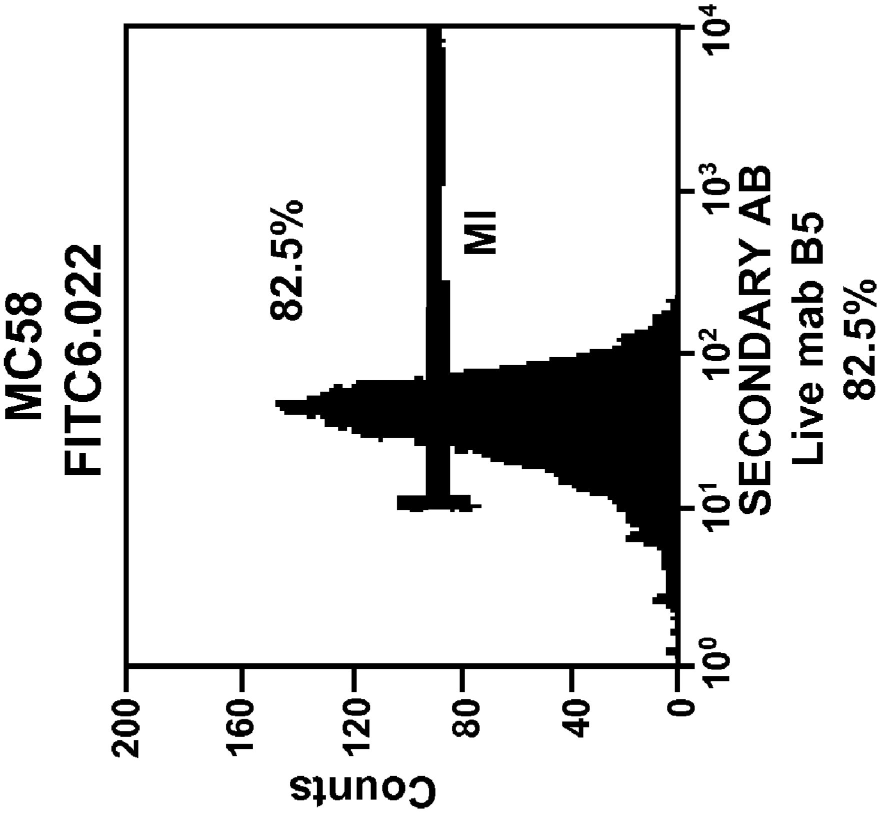
FIG. 15A illustrates a FACS profile showing surface labeling of live *Neisseria meningitidis* MC58 ($5\times10^8$ org./ml) with MAb B5 (culture supernatant 1:50) detected using anti-mouse IgG (FITC labelled).
Figure 15B:
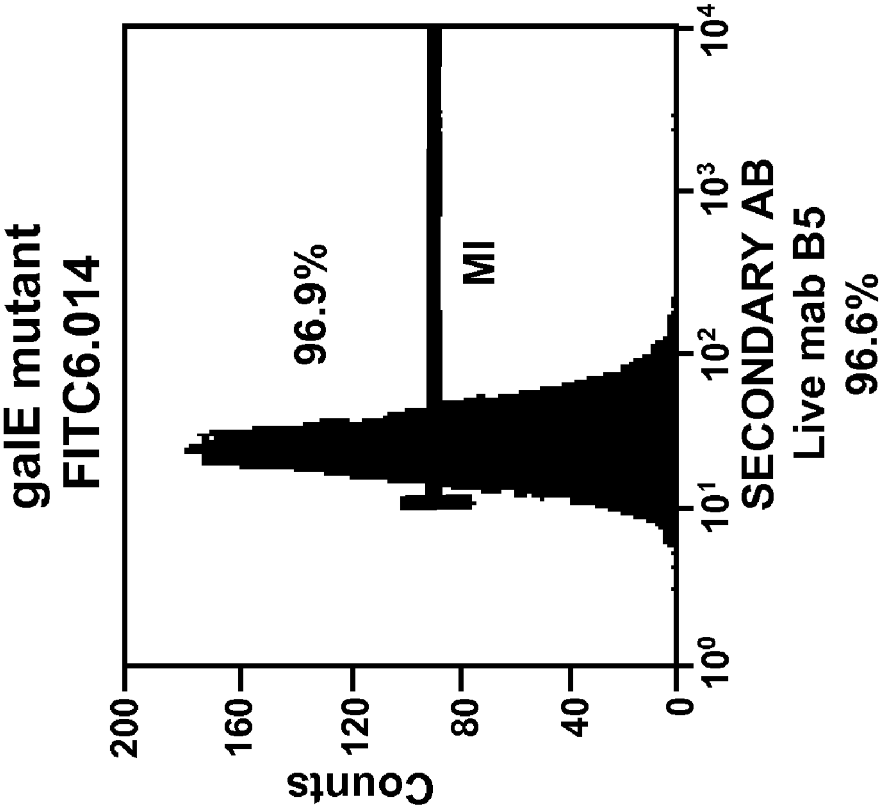
FIG. 15B illustrates a FACS profile comparing surface labeling of live *Neisseria meningitidis* galE mutant ($5\times10^8$ org./ml) with MAb B5 (culture supernatant 1:50) detected using anti-mouse IgG (FITC labeled).

MAb B5 binding to live wild-type strain MC58 and galE mutant, as shown in FIGS. 15A and 15B, respectively ($1\times10^8$ cfu/ml) were quantitatively compared using surface labeling with anti-mouse FITC and analyzed by FACS. The relative binding of MAb B5 to *Neisseria meningitidis* MC58 was 82.5% and *Neisseria meningitidis* galE mutant was 96.9% demonstrating that as expected the greatest binding was to the galE mutant but there was still significant binding to the wild-type strain MC58.

The invention claimed is:

1. A monoclonal antibody that binds to an epitope of the lipopolysaccharide (LPS) inner core of a galE mutant of an immunotype L3 strain of *Neisseria meningitidis*, wherein the LPS inner core epitope comprises a phosphoethanolamine moiety linked to the 3-position of HepII of the LPS inner core, wherein said monoclonal antibody binds to the LPS inner core of L1, L3, L7, L8, L9, L10, L11 and L12 immunotypes of *Neisseria meningitidis*, but not the LPS inner core of L2, L4, L5 and L6 immunotypes of *Neisseria meningitidis*, wherein the monoclonal antibody is the monoclonal antibody B5 produced by the hybridoma deposited with the accession number IDAC 260900-1.

* * * * *